United States Patent [19]

Chu et al.

[11] Patent Number: 5,071,848

[45] Date of Patent: Dec. 10, 1991

[54] TRICYCLIC QUINOLINE ANTINEOPLASTIC AGENTS

[75] Inventors: Daniel Tim-Wo Chu, Vernon Hills; Jacob J. Plattner; Linus L. Shen, both of Libertyville; Larry L. Klein, Lake Forest, all of Ill.

[73] Assignee: Abbott Laboratories, Abbott Park, Ill.

[21] Appl. No.: 425,536

[22] Filed: Oct. 23, 1989

[51] Int. Cl.[5] .................. A61K 31/495; A61K 31/54; A61K 31/535; A61K 31/55

[52] U.S. Cl. .................................... 514/218; 514/212; 514/228.5; 514/232.8; 514/254; 514/287; 514/293; 514/322; 540/575; 540/596; 540/597; 540/599; 544/58.1; 544/58.6; 544/60; 544/61; 544/125; 544/126; 544/361; 546/64; 546/83; 546/199

[58] Field of Search ............... 544/361, 60, 126, 58.1, 544/58.6, 61, 125; 540/596, 597, 575, 599; 546/83, 64, 199; 514/228.5, 232.8, 254, 293, 212, 218, 287, 322

[56] References Cited

U.S. PATENT DOCUMENTS 4,767,762 8/1988 Chu ..................................... 514/218
4,880,814 11/1989 Chu et al. ............................. 546/83

FOREIGN PATENT DOCUMENTS 1265092 10/1989 Japan ..................................... 546/83

OTHER PUBLICATIONS

R. B. Lock et al., Anti Cancer Drug Design (1987), 2, 151–164.
Peter D'Arpa et al., Biochimica et Biophysica Acta. 989 (1989) 163–177.
Lui, Annu. Rev. Biochem. 1989, 58-351-75.
Phillips et al., Drug Reviews, Clinical Pharmacy, vol. 2, 1983, pp. 112–119.

*Primary Examiner*—Cecilia Shen
*Attorney, Agent, or Firm*—Andreas M. Danckers; Steven F. Weinstock

[57] ABSTRACT

Isothiazolo-quinoline derivatives are described which are cytotoxic for various tumor cell lines and are useful in the treatment of neoplastic diseases.

15 Claims, No Drawings

TRICYCLIC QUINOLINE ANTINEOPLASTIC AGENTS

TECHNICAL FIELD

The compounds of the invention are isothiazolo-quinoline derivatives which have antineoplastic activity.

BACKGROUND OF THE INVENTION

It is known that certain tricyclic quinoline and naphthyridine derivatives possess antibacterial activities. For example, U.S. Pat. No. 4,767,762, incorporated herein by reference, discloses certain isothiazolo-quinoline derivatives which possess antibacterial activity. However, these and other related novel derivatives have not been known heretofore to be antineoplastic agents.

DNA topoisomerase I and DNA topoisomerase II are enzymes, located in the nuclei of cells, which bind to DNA and alter the configuration or topology of DNA. These enzymes play a key role in the replication, recombination and transcription of DNA necessary for cell growth and reproduction. Topoisomerases also play critical roles in maintaining chromosome and nuclear structure. Recently, several clinically useful antitumor agents were found to form cleavable complexes with DNA topoisomerases and DNA in tumor cells and to induce considerable DNA breakage. This damage to the DNA initiates a sequence of events that leads ultimately to the death of the tumor cell. Examples of clinically important antitumor drugs which have been found to affect the breakage-rejoining reaction of mammalian DNA mediated by DNA topoisomerases are anthracenediones such as mitoxantrone, and epipodophyllotoxins such as etoposide and teniposide. It was unexpectedly found that the compounds of the present invention, which are unrelated to known antitumor agents, can induce DNA breakage mediated by topoisomerase II and have cytotoxic activity.

SUMMARY OF THE INVENTION

The invention relates to compounds of Formula I having antineoplastic activity.

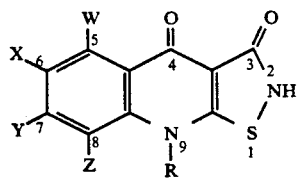

which may exist in its tautomeric form:

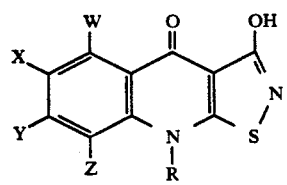

wherein R is selected from (a) lower alkyl, (b) haloalkyl, (c) lower cycloalkyl, (d) alkylamino, (e) an aromatic heterocyclic group and (f) a phenyl group; W, X and Z are independently selected from (a) hydrogen, (b) halogen and (c) lower alkyl; Y is selected from a phenyl group, a N-containing group, a bicyclic heterocyclic group and $OR_{10}$, wherein $R_{10}$ is hydrogen, lower alkyl or a phenyl group; or any two of W, X, Y and Z taken together form a fused, substituted or unsubstituted, aromatic group or heterocyclic group; and pharmaceutically acceptable salts, esters, amides and prodrugs thereof.

DETAILED DESCRIPTION OF THE INVENTION

The invention relates to compounds of Formula I and to a method of treating neoplastic diseases comprising administering to a patient in need a therapeutically effective amount of a compound of the formula:

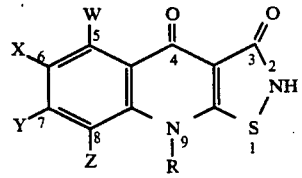

which may exist in its tautomeric form:

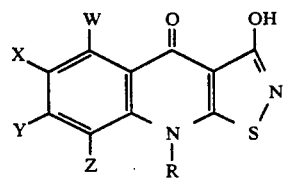

wherein Y is a N-containing group selected from amino groups having the following formula:

wherein $R_2$ and $R_3$ are independently selected from hydrogen, lower alkyl, arylalkyl, alkylamino, amino, aminoalkyl, hydroxy-substituted lower alkyl, a N-containing heterocyclic group and a bicyclic heterocyclic group, or alternately, $R_2$ and $R_3$ taken together may form a N-containing heterocyclic group having one or more heteroatoms selected from S, O and N with the remaining atoms being carbon. When $R_2$ and $R_3$ are taken together, the preferred heterocyclic groups are aliphatic heterocyclic rings having the formula:

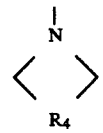

wherein $R_4$ is selected from $-(CH_2)_m-$ wherein m is 2 or 3 and $-(CH_2)_nR_5CH_2$ wherein $R_5$ is selected from S, O and N and n is 1 or 2. Also included are substituted derivatives of such heterocyclic groups wherein the number of substituents is one, two or three and they are independently selected from lower alkyl, aminoalkyl, hydroxy-substituted lower alkyl, lower alkoxy, hydroxy, halogen, alkanoylamino and an amino group having the formula:

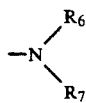

wherein R₆ and R₇ are independently selected from hydrogen, lower alkyl, α-amino acid and polypeptide residues of 2-5 amino acids.

Alternately, Y is a substituted or unsubstituted bicyclic heterocyclic group having the formula:

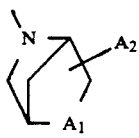

wherein A₁ is a heteroatom selected from S, O and N and A₂ is selected independently from one or more of the following: lower alkyl, hydroxy-substituted lower alkyl, a phenyl group, aminoalkyl, hydroxy, halogen, alkanoylamino, and an amino group having the following formula:

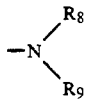

wherein R₈ and R₉ are independently selected from hydrogen, lower alkyl, α-amino acid, and polypeptide residues of 2-5 amino acids.

Y can also be a phenyl group which may be substituted by one to three substituents selected independently from lower alkyl, halogen, hydroxy, hydroxy substituted lower alkyl, amino, alkylamino, and aminoalkyl or Y can be OR₁₀, wherein R₁₀ is hydrogen, lower alkyl or a phenyl group.

W, X and Z are independently selected from hydrogen, halogen and lower alkyl; or any two of W, X, Y and Z taken together form a fused, substituted or unsubstituted, aromatic group or heterocyclic group. R is (a) lower alkyl, (b) haloalkyl, (c) lowercycloalkyl, (d) alkylamino, (e) an aromatic heterocyclic group or (f) a phenyl group.

The present invention also relates to compositions comprising a therapeutically effective amount of the compounds of Formula I or II and a pharmaceutically acceptable carrier or diluent.

The preferred compounds of the invention are those having the Formula I wherein R is cyclopropyl, ethyl, phenyl or substituted phenyl wherein the substituents on the phenyl ring are one or more halogen, hydroxy, or two substituents taken together can form a methylenedioxy ring; W is hydrogen; X and Z are halogen or X is halogen and Z is hydrogen; and Y is piperazinyl, substituted piperazinyl, piperidinyl, substituted piperidinyl, aminopyrrolidinyl, substituted aminopyrrolidinyl, morpholino, thiomorpholino or substituted phenyl as described above.

The chiral centers of the compounds may have either the R or S configuration.

Representative of the preferred compounds are:

9-cyclopropyl-6,8-difluoro-7-(1-piperazinyl)-2,3,4,9-tetrahydroisothiazolo[5,4-b]quinoline-3,4-dione;
9-cyclopropyl-6,8-difluoro-7-(3-methyl-1-piperazinyl)-2,3,4,9-tetrahydroisothiazolo[5,4-b]quinoline-3,4-dione;
9-cyclopropyl-6,8-difluoro-7-(4-methyl-1-piperazinyl)-2,3,4,9-tetrahydroisothiazolo[5,4-b]quinoline-3,4-dione;
9-cyclopropyl-6,8-difluoro-7-(4-(2'-hydroxy)ethyl-1-piperazinyl)-2,3,4,9-tetrahydroisothiazolo[5,4-b]quinoline-3,4-dione;
9-cyclopropyl-6,8-difluoro-7-(1-piperidinyl)-2,3,4,9-tetrahydroisothiazolo[5,4-b]quinoline-3,4-dione;
9-cyclopropyl-6,8-difluoro-7-(4-hydroxy-1-piperidinyl)-2,3,4,9-tetraphydroisothiazolo[5,4-b]quinoline-3,4-dione;
9-cyclopropyl-6,8-difluoro-7-(1-morpholino)-2,3,4,9-tetrahydroisothiazolo[5,4-b]quinoline-3,4-dione;
9-cyclopropyl-6,8-difluoro-7-(1-thiomorpholino)-2,3,4,9-tetrahydroisothiazolo[5,4-b]quinoline-3,4-dione;
9-cyclopropyl-6,8-difluoro-7-(1-diazepinyl)-2,3,4,9-tetrahydroisothiazolo[5,4-b]quinoline-3,4-dione;
9-cyclopropyl-6,8-difluoro-7-(3-amino-1-pyrrolidinyl)-2,3,4,9-tetrahydroisothiazolo[5,4-b]quinoline-3,4-dione;
9-cyclopropyl-6,8-difluoro-7-(3-aminomethyl-1-pyrrolidinyl)-2,3,4,9-tetrahydroisothiazolo[5,4-b]quinoline-3,4-dione;
9-cyclopropyl-6,8-difluoro-7-(4-chloro-3-aminomethyl-1-pyrrolidinyl)-2,3,4,9-tetrahydroisothiazolo[5,4-b]quinoline-3,4-dione;
9-cyclopropyl-6,8-difluoro-7-(1-piperazinyl)-2,3,4,9-tetrahydroisothiazolo[5,4-b]quinoline-3,4-dione;
9-cyclopropyl-6,8-difluoro-7-(3-ethylaminomethyl-1-pyrrolidinyl)-2,3,4,9-tetrahydroisothiazolo[5,4-b]quinoline-3,4-dione;
9-cyclopropyl-6,8-difluoro-7-(N-valyl-3-amino-1-pyrrolidinyl)-2,3,4,9-tetrahydroisothiazolo[5,4-b]quinoline-3,4-dione;
9-cyclopropyl-6,8-difluoro-7-(N-alanyl-3-amino-1-pyrrolidinyl)-2,3,4,9-tetrahydroisothiazolo[5,4-b]quinoline-3,4-dione;
9-cyclopropyl-6,8-difluoro-7-(N-glycyl-3-amino-1-pyrrolidinyl)-2,3,4,9-tetrahydroisothiazolo[5,4-b]quinoline-3,4-dione;

9-ethyl-6,8-difluoro-7-(1-piperazinyl)-2,3,4,9-tetrahydroisothiazolo[5,4-b]quinoline-3,4-dione;
9-ethyl-6,8-difluoro-7-(3-methyl-1-piperazinyl)-2,3,4,9-tetrahydroisothiazolo[5,4-b]quinoline-3,4-dione;
9-ethyl-6,8-difluoro-7-(4-methyl-1-piperazinyl)-2,3,4,9-tetrahydroisothiazolo[5,4-b]quinoline-3,4-dione;
9-ethyl-6,8-difluoro-7-(4-(2'-hydroxy)ethyl-1-piperazinyl)-2,3,4,9-tetrahydroisothiazolo[5,4-b]quinoline-3,4-dione;
9-ethyl-6,8-difluoro-7-(1-piperidinyl)-2,3,4,9-tetrahydroisothiazolo[5,4-b]quinoline-3,4-dione;
9-ethyl-6,8-difluoro-7-(4-hydroxy-1-piperidinyl)-2,3,4,9-tetrahydroisothiazolo[5,4-b]quinoline-3,4-dione;
9-ethyl-6,8-difluoro-7-(1-morpholino)-2,3,4,9-tetrahydroisothiazolo[5,4-b]quinoline-3,4-dione;
9-ethyl-6,8-difluoro-7-(1-thiomorpholino)-2,3,4,9-tetrahydroisothiazolo[5,4-b]quinoline-3,4-dione;
9-ethyl-6,8-difluoro-7-(1-diazepinyl)-2,3,4,9-tetrahydroisothiazolo[5,4-b]quinoline-3,4-dione;

9-ethyl-6,8-difluoro-7-(3-amino-1-pyrrolidinyl)-2,3,4,9-tetrahydroisothiazolo[5,4-b]quinoline-3,4-dione;

9-ethyl-6,8-difluoro-7-(3-aminomethyl-1-pyrrolidinyl)-2,3,4,9-tetrahydroisothiazolo[5,4-b]quinoline-3,4-dione;

9-ethyl-6,8-difluoro-7-(4-chloro-3-aminomethyl-1-pyrrolidinyl)-2,3,4,9-tetrahydroisothiazolo[5,4-b]quinoline-3,4-dione;

9-ethyl-6,8-difluoro-7-(1-piperazinyl)-2,3,4,9-tetrahydroisothiazolo[5,4-b]quinoline-3,4-dione;

9-ethyl-6,8-difluoro-7-(3-ethylaminomethyl-1-pyrrolidinyl)-2,3,4,9-tetrahydroisothiazolo[5,4-b]quinoline-3,4-dione;

9-ethyl-6,8-difluoro-7-(N-valyl-3-amino-1-pyrrolidinyl)-2,3,4,9-tetrahydroisothiazolo[5,4-b]quinoline-3,4-dione;

9-ethyl-6,8-difluoro-7-(N-alanyl-3-amino-1-pyrrolidinyl-2,3,4,9-tetrahydroisothiazolo[5,4-b]quinoline-3,4-dione;

9-ethyl-6,8-difluoro-7-(N-glycyl-3-amino-1-pyrrolidinyl)-2,3,4,9-tetrahydroisothiazolo[5,4-b]quinoline-3,4-dione;

9-cyclopropyl-6-fluoro-7-(1-piperazinyl)-2,3,4,9-tetrahydroisothiazolo[5,4-b]quinoline-3,4-dione;

9-cyclopropyl-6-fluoro-7-(3-methyl-1-piperazinyl)-2,3,4,9-tetrahydroisothiazolo[5,4-b]quinoline-3,4-dione;

9-cyclopropyl-6-fluoro-7-(4-methyl-1-piperazinyl)-2,3,4,9-tetrahydroisothiazolo[5,4-b]quinoline-3,4-dione;

9-cyclopropyl-6-fluoro-7-(4-(2'-hydroxy)ethyl-1-piperazinyl)-2,3,4,9-tetrahydroisothiazolo[5,4-b]quinoline-3,4-dione;

9-cyclopropyl-6-fluoro-7-(1piperidinyl)-2,3,4,9-tetrahydroisothiazolo[5,4-b]quinoline-3,4-dione;

9-cyclopropyl-6-fluoro-7-(4-hydroxy-1-piperidinyl)-2,3,4,9-tetrahydroisothiazolo[5,4-b]quinoline-3,4-dione;

9-cyclopropyl-6-fluoro-7-(1-morpholino)-2,3,4,9-tetrahydroisothiazolo[5,4-b]quinoline-3,4-dione;

9-cyclopropyl-6-fluoro-7-(1-thiomorpholino)-2,3,4,9-tetrahydroisothiazolo[5,4-b]quinoline-3,4-dione;

9-cyclopropyl-6-fluoro-7-(1-diazepinyl)-2,3,4,9-tetrahydroisothiazolo[5,4-b]quinoline-3,4-dione;

9-cyclopropyl-6-fluoro-7-(3-amino-1-pyrrolidinyl)-2,3,4,9-tetrahydroisothiazolo[5,4-b]quinoline-3,4-dione;

9-cyclopropyl-6-fluoro-7-(3-aminomethyl-1-pyrrolidinyl)-2,3,4,9-tetrahydroisothiazolo[5,4-b]quinoline-3,4-dione;

9-cyclopropyl-6-fluoro-7-(4-chloro-3-aminomethyl-1-pyrrolidinyl)-2,3,4,9-tetrahydroisothiazolo[5,4-b]quinoline-3,4-dione;

9-cyclopropyl-6-fluoro-7-(1-piperazinyl)-2,3,4,9-tetrahydroisothiazolo[5,4-b]quinoline-3,4-dione;

9-cyclopropyl-6-fluoro-7-(3-ethylaminomethyl-1-pyrrolidinyl)-2,3,4,9-tetrahydroisothiazolo[5,4-b]quinoline-3,4-dione;

9-cyclopropyl-6-fluoro-7-(N-valyl-3-amino-1-pyrrolidinyl)-2,3,4,9-tetrahydroisothiazolo[5,4-b]quinoline-3,4-dione;

9-cyclopropyl-6-fluoro-7-(N-alanyl-3-amino-1-pyrrolidinyl)-2,3,4,9-tetrahydroisothiazolo[5,4-b]quinoline-3,4-dione;

9-cyclopropyl-6-fluoro-7-(N-glycyl-3-amino-1-pyrrolidinyl)-2,3,4,9-tetrahydroisothiazolo[5,4-b]quinoline-3,4-dione;

and pharmaceutically acceptable salts, esters, amides or prodrugs thereof.

As used herein, the term "halogen" refers to chloro (Cl), bromo (Br), fluoro (F) and iodo (I).

The term "lower alkyl" refers to branched or straight chain lower alkyl groups containing 1-5 carbon atoms including, but not limited to, methyl, ethyl, propyl, isopropyl, n-butyl, t-butyl, neopentyl and the like.

The term "lower cycloalkyl" refers to $C_3$ to $C_6$ cycloalkyl groups including, but not limited to, cyclopropyl, cyclobutyl, cyclopentyl and cyclohexyl.

The term "phenyl group" refers to either unsubstituted benzene rings or to benzene rings bearing one to three non-hydrogen substituents independently selected from the group consisting of halogen, hydroxy, lower alkoxy, lower alkyl, hydroxy-substituted lower alkyl, amino, alkylamino and aminoalkyl.

The term "arylalkyl" refers to an aromatic group, such as a phenyl group, which is bonded to a lower alkyl group. Examples of arylalkyl groups are benzyl and phenylethyl groups.

The term "aromatic group" refers to a $C_6$ to $C_{10}$ cyclic group which is aromatic according to Huckel's rule, for example phenyl and naphthyl.

The term "fused" as used herein refers to two cyclic groups having two atoms in common to both rings.

The term "heterocyclic group" as used herein refers to a 5 to 7 atom cyclic group containing between one and three heteroatoms selected from S, O or N. The cyclic group may be unsubstituted or it may be substituted, either on a heteroatom or on a carbon atom, with for example, arylalkyl, lower alkyl, aminoalkyl, hydroxy-substituted lower alkyl, hydroxy, lower alkoxy, halogen, amino, alkylamino, alkanoylamino, an α-amino acid or a polypeptide of 2–5 amino acids.

The term "aromatic heterocyclic group" refers specifically to a 5 to 7 atom cyclic group containing between one and three heteroatoms such as S, O or N with the remaining atoms being carbon, which is aromatic according to Huckel's rule. These heterocycles may be unsubstituted or they may be substituted for example with lower alkyl, providing that any such substituents not interfere with the efficacy of the compound.

The term "N-containing heterocyclic group" refers to a "heterocyclic group" as defined above wherein at least one of the heteroatoms is nitrogen.

The term "N-containing group" refers to an amino group having the following formula:

wherein $R_2$ and $R_3$ are independently selected from hydrogen, lower alkyl, arylalkyl, hydroxy-substituted lower alkyl, alkylamino, amino, aminoalkyl, a N-containing heterocyclic group and a bicyclic N-containing heterocyclic group, or wherein $R_2$ and $R_3$ taken together form a N-containing heterocyclic group having between one and three heteroatoms selected from S, O and N with the remaining atoms being carbon. Also included are substituted derivatives of such heterocyclic groups wherein the number of substituents is one, two or three and they are independently selected from lower alkyl, aminoalkyl, hydroxy-substituted lower alkyl, lower alkoxy, hydroxy, halogen, alkanoylamino and an amino group having the formula:

wherein $R_6$ and $R_7$ are independently selected from hydrogen, lower alkyl, α-amino acid, and polypeptide residues of 2-5 amino acids.

The term "bicyclic N-containing heterocyclic group" refers to a group of the formula:

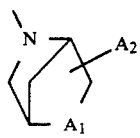

wherein $A_1$ is a heteroatom selected from S, O and N and $A_2$ is selected independently from between one and three of the following: lower alkyl, hydroxy-substituted lower alkyl, a phenyl group, hydroxy, halogen, aminoalkyl, alkanoylamino and an amino group having the following formula:

wherein $R_8$ and $R_9$ are independently selected from hydrogen, lower alkyl, α-amino acid and polypeptide residues of 2-5 amino acids.

The term "haloalkyl" refers to a lower alkyl group, as defined above, bearing at least one halogen substituent, for example, fluoroethyl.

The term "hydroxy-substituted lower alkyl" refers to lower alkyl groups, as defined above, having at least one hydroxyl substituent, for example hydroxyethyl.

The term "lower alkoxy" refers to a lower alkyl group, as defined above, which is bonded through an oxygen atom. Examples of lower alkoxy groups include methoxy, ethoxy, t-butoxy and the like.

The term "alkylamino" refers to amino groups substituted with one to three lower alkyl groups, including, but not limited to, methylamino and ethylmethylamino.

The term "aminoalkyl" refers to lower alkyl groups, as defined above, having at least one amino substituent, which may have one or two lower alkyl substituents. Examples of aminoalkyl groups include aminoethyl, aminomethyl, N,N-dimethylaminoethyl and the like.

The term "alkanoylamino" refers to a substituent of the formula $R_{11}C(O)NH$— wherein $R_{11}$ is a lower alkyl group, as defined above, and includes, but is not limited to acetylamino and pivaloylamino.

The terms "α-amino acid" and "polypeptide residue" refer to a single amino acid or two or more amino acids joined by amide (peptide) bonds. The amino acids can be naturally occurring amino acids such as valine or glycine or they may be synthetic α-amino acids such as cyclohexylalanine. The amino acids can either be in the L or D configuration or a mixture of the two isomers. If not specified, amino acid substituents are optically active and have the L configuration.

The term "prodrug" refers to compounds that rapidly hydrolyze in blood to yield parent compound of the Formula I or II.

The term "neoplastic diseases" refers to disorders and disease states characterized by abnormal proliferative growth of cells, such as leukemias; lymphomas; myelomas; melanoma; sarcomas; blastomas and tumors for example, of the head, thyroid, neck, brain, esophagus, lung, breast, stomach, pancreas, genitourinary tract; and the like. Antineoplastic agents are chemical compounds which are effective in the treatment of any one or more neoplastic disease. Chemotherapy of neoplastic diseases is discribed in "Goodman and Gilman's The Pharmacological Basis of Therapeutics", seventh edition, A. G. Gilman, et al. eds., pp 1240-1306 (1985).

Also included within the scope of the present invention are pharmaceutically acceptable salts, esters and amides of the compounds of Formulas I and II. The salts can be prepared in situ during the final isolation and purification of the compounds or separately by reacting the free base, acid or hydroxy functions with a suitable organic acid or base.

By "pharmaceutically acceptable" is meant those salts and esters which are, within the scope of sound medical judgement, suitable for use in contact with the tissues of humans and lower animals without undue toxicity, irritation, allergic response, and the like, commensurate with a reasonable benefit/risk ratio, and effective for their intended use.

Examples of pharmaceutically acceptable, nontoxic acid addition salts are salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Other pharmaceutically acceptable salts include nitrate, bisulfate, borate, formate, valerate, benzoate, oleate, palmitate, stearate, laurate, lactate, fumerate, ascorbate, p-toluenesulfonate, mesylate, glucoheptonate, lactobionate, lauryl sulfate, and the like or metal salts such as sodium, potassium magnesium or calcium salts or amino salts such as ammonium, triethylamine salts, and the like and they may be prepared according to conventional methods.

Examples of pharmaceutically acceptable, non-toxic esters of the compounds of formula I include $C_1$ to $C_6$ alkyl esters wherein the alkyl group is straight or branched chain. Acceptable esters also include $C_5$ to $C_7$ cycloalkyl esters. $C_1$ to $C_4$ alkyl esters are preferred. Esters of the compounds of formula I may be prepared according to conventional methods.

Examples of pharmaceutically acceptable, nontoxic amides of the compounds of formula I include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compounds of formula I may be prepared according to conventional methods. It is understood that amides of the compounds of the present invention include amino acid and peptide derivatives.

The compounds of the present invention may be administered orally, parenterally, by inhalation spray, rectally, or topically in dosage form unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

The daily dosage of the compounds of the present invention may be suitably defined according to the condition of the patient by those skilled in the art but generally may be administered in an amount of about 0.1–750 mg/kg body weight, more preferably about 0.25–500 mg/kg, and most preferably about 0.5 to about 300 mg of active ingredient per kg. of body weight. Dosage unit compositions may contain such amounts of submultiples thereof to make up the daily dose.

The amount of active ingredient that may be combined with carrier material to produce a single dosage form will vary depending upon the host treated and the particular mode of administration.

It will be understood, however, that the specific dose level for any particular patient will depend upon a variety of factors including the activity of the specific compound employed; the age, body weight, general health, sex and diet of the patient; the time of administration; the route of administration; the rate of excretion; any drug combination used; and the severity of the particular disease undergoing therapy.

As used herein, the term "pharmaceutically acceptable carriers" means a solid or liquid filler, diluent or encapsulating material. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl celulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the desires of the formulator.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Suppositories for rectal or vaginal administration of the drug can be prepared by mixing the drug with a suitable nonirritating excipient such as cocoa butter and polyethylene glycol which are solid at ordinary temperature but liquid at the rectal temperature and will therefore melt in the rectum or vagina and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Liquid dosage forms for oral administration may include pharmaceutically acceptable emulsions, microemulsions, solutions, suspensions, syrups and elixirs containing inert diluent commonly used in the art such as water. Such compositions may also comprise adjuvants, such as wetting agents; emulsifying and suspending agents; sweetening, flavoring and perfuming agents.

If desired, the compounds of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can dissolve in sterile water, or some other sterile injectable medium immediately before use.

The active compounds can also be in micro-encapsulated form with one or more excipients as noted above.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Compounds according to this invention can be prepared by the following schemes I and II in which W, X, Y, Z, and R are as defined for Formulas I and II, and L is a leaving group, preferably a fluorine or chlorine atom and $R_{12}$ and $R_{13}$ are lower alkyl groups or a phenyl group.

the β-ketoester (3) with a base such as sodium hydride in an aprotic solvent such as tetrahydrofuran (THF) or N,N-dimethylformamide (DMF) with a substituted isothiocyanate (4) at 0° to 40° C. for 3 to 36 hours, followed by the addition of an alkyl halide such as methyl iodide yields the enaminoketoester (5). The

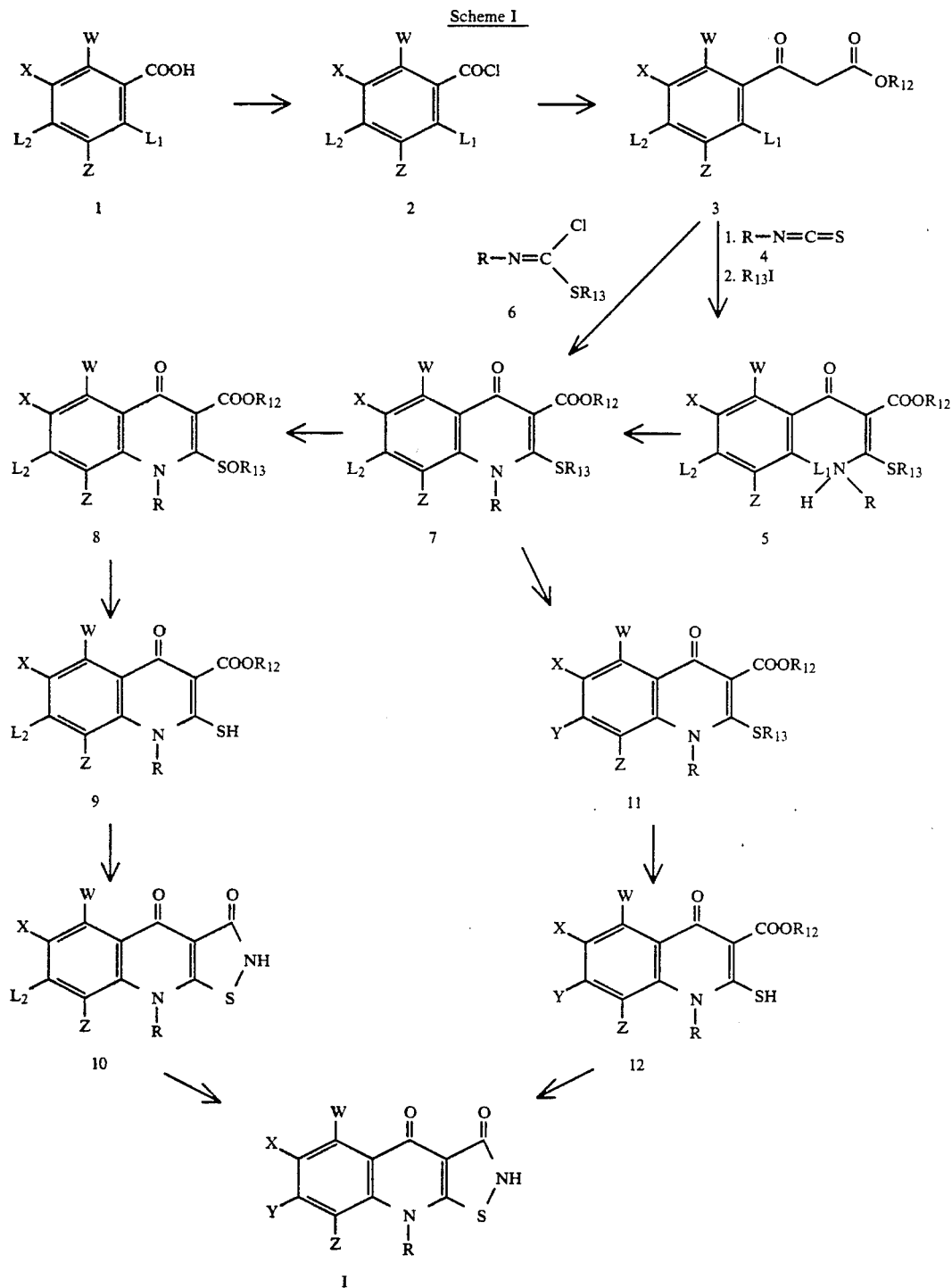

Scheme I

In accordance with the foregoing reaction scheme, the substituted benzoic acid (1) is converted to its acid chloride (2) by treatment with a chlorinating agent such as thionyl chloride. Displacement of the chloride with malonic acid half ester in the presence of a base such as n-butyl lithium yields the β-keto ester (3). Treatment of latter reaction may be conducted at ambient temperature or suitable elevated temperature, as desired.

The enaminoketoester (5) is then cyclized, such as by treatment with a strong base, preferably sodium hydride, to obtain the 1,4-dihydro-4-oxo-quinoline-3-carboxylic acid ester (7). Cyclization is conducted in an aprotic solvent, such as dimethoxyethane, bis(2-methoxyethyl)ether, dimethylformamide (DMF), THF or chlorobenzene, and is preferably conducted at temperatures of about 20° C. to about 145° C., more preferably at the reflux temperature of the solvent employed.

Alternately, the 3-carboxylic acid ester (7) can be prepared by treatment of the β-ketoester (3) in the presence of a base such as sodium hydride in an aprotic solvent, preferably THF or toluene, with an alkyl or phenyl N-substituted iminochlorothioformate (6) at ambient temperature or suitable elevated temperature as desired.

Oxidation of the 3-carboxylic acid ester (7), for example with metachloroperoxybenzoic acid (mCPBA) in a nonpolar solvent such as methylene chloride or chloroform, yields the sulfoxide (8). The reaction may be conducted at a temperature from 0° C. to 50° C.

Reaction of (8) with sodium hydrosulfide in an aprotic solvent, preferably aqueous THF, at elevated temperature yields the 2-mercapto-derivative (9). Treatment of (9) with hydroxylamine-O-sulfonic acid in the presence of a base, preferably sodium bicarbonate in a protic solvent, preferably aqueous THF, yields the isothiazolo derivative (10).

Displacement of the 7-leaving group of (10) with an amine yields the 7-amino-substituted isothiazolo derivatives (I). The reaction may be conducted at a temperature from 20° C. to 130° C. in a suitable organic solvent such as pyridine, methylene chloride, chloroform or 1-methyl-2-pyrrolidinone. It is desirable to carry out the reaction in the presence of an acid-acceptor such as triethylamine, potassium carbonate and the like, at a molar ratio of 1.0 to 2.0 moles of the acid acceptor per mole of compound of the formula (10). The amine can also be used as an acid acceptor in which case 2 or more equivalents of this reagent is used.

Alternately, the 7-leaving group of compound (7) is displaced by an amino group yielding the 7-amino derivative (11). The displacement reaction is carried out as described above. Reaction of (11) with sodium hydrosulfide in a protic solvent, preferably aqueous THF, at elevated temperature yields the 2-mercapto-derivative (12). Treatment of (12) with hydroxylamine-O-sulfonic acid in the presence of a base, preferably sodium bicarbonate, in a protic solvent, preferably aqueous THF, yields compounds of the formula I.

In the case where Y is a phenyl group, the compound (11) is formed by coupling the compound (7) with an aryl metal compound, for example, phenyl lithium, at the 7-position to replace the 7-leaving group with a phenyl group. The coupling reaction is carried out in a reaction-inert solvent, i.e., a solvent which does not interfere with the coupling reaction of the aryl metal compound with compound (7). In this case compounds 11, 12 and I are represented by a formula wherein the Y group is 7-phenyl or substituted phenyl. Suitable reaction-inert solvents include ethers, for example diethyl ether, dimethoxyethane and THF. Co-solvents may be used with ethers if desired. These co-solvents may be benzene, toluene, tetramethylethyleneamine (TMEDA) and hexamethylphosphorictriamide (HMPA).

The aryl metal compounds may be prepared by known methods. For example, they may be prepared by direct lithium-halogen exchange of the corresponding arylhalide using n-butyl, sec-butyl or t-butyl lithium followed by transmetallation by a wide variety of salts by known methods such as described by E. Negishi in "Organometallics in Organic Synthesis", Vol. 1, page 104.

The compounds of this invention are also prepared as described herein in Scheme II.

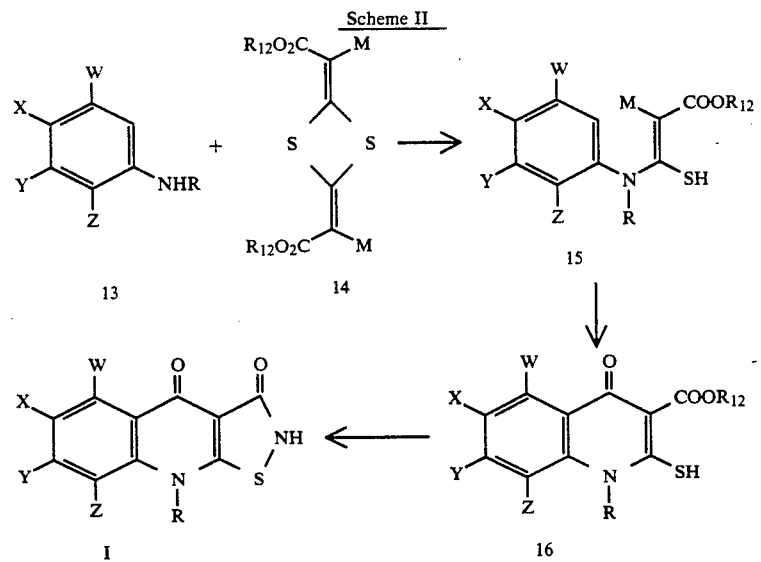

Scheme II

In accordance with the foregoing reaction scheme an aromatic amine derivative (13) is reacted with reagent (14: wherein $R_{12}$ is defined for Scheme I and M is an electron-withdrawing group such as $CO_2R_{12}$, CN or C(O)NRR', wherein R and R' are selected from hydrogen and lower alkyl) at temperatures from 25° C. to 50° C. in a suitable organic solvent such as acetonitrile, THF or toluene. The product of this reaction (15) is then heated in a high-boiling nonpolar solvent such as diphenyl ether or biphenyl-phenyl ether mixture, sold under the registered trademark Dowtherm A ® by Dow Chemical Company, for 1–3 h or heated to 120° C. in polyphosphoric acid for 1–3 h. Treatment of (16) with hydroxylamine-O-sulfuric acid as described above for compound (9) then affords the desired product (I).

The foregoing may be better understood from the following examples, which are presented for the purposes of illustration and are not intended to limit the scope of the inventive concept.

EXAMPLE 1

9-Cyclopropyl-6,8-difluoro-7-(1-morpholino)-2,3,4,9-tetrahydroisothiazolo[5,4-b]quinoline-3,4-dione

Step 1: Preparation of phenyl N-cyclopropyliminochlorothioformate a) Carbon disulfide (79.18 mL, 1.31 mol) was added to a solution of 51.8 g (1.30 mol) of sodium hydroxide in 1.6 mL of water at 0° C. After stirring this solution for 10 minutes at 0° C., 74 g (1.30 mol) of cyclopropylamine was added dropwise over a 30 minute period. The reaction mixture was heated at 65° C. for 2 h then allowed to stand overnight at ambient temperature. To the solidified reaction mixture was added 119.8 mL (136 g, 1.25 mol) of ethyl chloroformate portionwise over a one hour period. During the addition gas evolution was observed and heat was produced. After addition was complete, the reaction mixture was heated at 65° C. for approximately 7 h then stirred at ambient temperature over the weekend. The reaction mixture was then extracted with diethyl ether and the ether extract was concentrated under reduced pressure. An additional 6 mL (63 mmol) aliquot of ethyl chloroformate and 0.5 mL of triethylamine were added and the reaction mixture was heated at 65° C. for 3 h. The solvent was removed under reduced pressure and the crude product distilled to give 67.5 g (51.83% yield) of N-cyclopropyl thioisocyanate, b.p. 53°–58° C. (~8 mm Hg).

b) The N-cyclopropyl thioisocyanate (67 g, 676 mmol) from Step 1a and 67.3 mL (0.97 equivalents) of thiophenol were mixed together at ambient temperature. To this mixture was added 4 drops of triethylamine. Upon addition of the amine, the reaction mixture became pale yellow and heat evolution was observed for 2 h. The reaction was cooled in an ice bath and the resultant solid was dissolved in chloroform. The chloroform was removed under reduced pressure and hexane was added to the residual liquid. Upon cooling the hexane solution in an ice bath, a precipitate formed which was filtered and washed with hexane to give 120 g (84.84% yield) of N-cyclopropyliminomercaptothioformate and this was taken on without purification.

c) The N-cyclopropyliminomercaptothioformate (65 g, 310 mmol) from Step 1b (a white solid) and 64.6 g (0.98 equivalents) of phosphorous pentachloride (a white solid) were combined at ambient temperature and stirred. After stirring for 3 minutes at ambient temperature an orange color was observed and after 1 h the reaction mixture was a suspension. The reaction mixture was then heated on a hot plate at 65° C. for 6 h. The hydrogen chloride and thiophosphoryl chloride by-products were removed in vacuo and the residual liquid distilled to give 56 g (85.17% yield) of N-cyclopropyliminochlorothioformate as a golden yellow oil, b.p. 85°–90° C. (0.3 mm Hg).

Step 2: 1-Cyclopropyl-1,4-dihydro-3-ethoxycarbonyl-2-phenylthio-6,7,8-trifluoroquinoline-4-one A suspension of ethyl 2,3,4,5-tetrafluorobenzoylacetate (20 g, 75.8 mmol), prepared as described by D. T. W. Chu and R. E. Maleczka, Jr. in *J. Heterocyclic Chem*, 24, 453–456 (1987), and sodium hydride (3.18 g of 60% NaH in mineral oil, 1.05 equivalents) in 270 mL of toluene was stirred for 40 minutes. Phenyl N-cyclopropyliminochlorothioformate (19.4 g, 1.21 equivalents) from Step 1 was then added in one portion and the reaction mixture was stirred at ambient temperature for 1 h, then heated at 100° C. for 16 h. The solvent was evaporated in vacuo and the residual oil was partitioned between a mixture of 1 part chloroform and 3 parts saturated aqueous ammonium chloride solution. The layers were separated and the chloroform was removed from the organic phase under reduced pressure. The resultant oily residue was purified by column chromatography on silica gel (150 g) eluted with a gradient 30%–50% diethyl ether in methylene chloride to yield the title compound which was recrystallized from 25% ethyl acetate in hexanes to give 14 g (44% yield) of the desired product, m.p. 135°–137° C. $^1$H NMR (CDCl$_3$) $\delta$7.87 (m, 1H, H$_5$), 7.36–7.45 (m, 5H, Ph), 4.37 (q, 2H, OCH$_2$), 2.88 (m, 1H, NCH), 1.35 (t, 3H, OCH$_2$CH$_3$), 1.18 (d, 2H, cyclopropyl), 0.92 (br s, 2H, cyclopropyl).

Step 3: 1-Cyclopropyl-1,4 dihydro-3-ethoxycarbonyl-2-phenylsulfinyl-6,7,8-trifluoroquinoline-4-one A solution of 1-cyclopropyl-1,4-dihydro-3-ethoxycarbonyl-2-phenylthio-6,7,8-trifluoroquinoline-4-one (13.3 g, 31.7 mmol) from Step 2 and 3-chloroperoxybenzoic acid (11 g of Aldrich 50–60% peroxy acid, 1.1 equivalents) in 300 mL of chloroform was heated at 45° C. for 1 h and stirring was continued at ambient temperature for 3 h. The reaction mixture was washed twice with 1M aqueous sodium carbonate solution and concentrated under reduced pressure. The resultant oil was purified by column chromatography on silica gel (400 g) eluted with 10% methanol in methylene chloride to give 12 g (87% yield) of the title compound, m.p. 190°–191° C. (after recrystallization from 30% ethyl acetate in hexanes). $^1$H NMR (CDCl$_3$) $\delta$7.95–8.00 (m, 2H, Ph), 7.86–7.93 (m, 1H, H$_5$), 5.52–7.62 (m, 3H, Ph), 4.40–4.55 (m, 2H, OCH$_2$), 3.46 (m, 1H, NCH), 1.42 (t, 3H, OCH$_2$CH$_3$), 0.8–1.38 (m, 4H, cyclopropyl).

Step 4: 9-Cyclopropyl-6,7,8-trifluoro-2,3,4,9-tetrahydroisothiazolo[5,4-b]quinoline-3,4-dione A suspension of 1-cyclopropyl-3-ethoxycarbonyl-2-phenylsulfinyl-6,7,8-trifluoroquinoline-4-one (12 g, 27.6 mmol) from Step 3 and 4.6 g of sodium hydrosulfide hydrate (NaSH) in 300 mL of tetrahydrofuran (THF) was stirred for 40 minutes at 0° C. A solution of sodium bicarbonate (4 g, 47.6 mmol) in 20 mL of water was added and the resultant brownish solution was stirred for 2 h at 0° C. To this solution, containing crude 1-cyclopropyl-3-ethoxycarbonyl-2-mercapto-6,7,8-trifluoroquinoline-4-one, was added 7 g (61.9 mmol) of hydroxylamine-O-sulfonic acid, followed by a solution of 12 g (142 mmol) of sodium bicarbonate in 60 mL of water. The reaction mixture was warmed to ambient temperature and stirring was continued for 2.5 h. The solvents were evaporated in vacuo and the gummy residue was triturated three times with diethyl ether. The ether was decanted and a yellow paste, containing the sodium salt of the desired product was obtained. The yellow paste was suspended in 2M aqueous hydrochloric acid solution. The resultant insoluble solid was filtered, heated in ethanol and refiltered to give 7.05 g (82% yield) of the title compound, m.p. 243°–245° C. $^1$H NMR (CDCl$_3$) $\delta$9.6–9.9 (br s, 1H, NH), 8.03–8.11 (m, 1H, H5), 3.82 (m, 1H, NCH), 1.2–1.4 (m, 4H, cyclopropyl).

Step 5:
9-Cyclopropyl-6,8-difluoro-7-(1-morpholino)-2,3,4,9-tetrahydroisothiazolo[5,4-b]quinoline-3,4-dione A solution of 9-cyclopropyl-6,7,8-trifluoro-2,3,4,9-tetrahydroisothiazolo[5,4-b]quinoline-3,4-dione (3.17 g, 10.2 mmol) from Step 4 and 2.7 mL (3 equivalents) of morpholine in 31 mL of pyridine was stirred at ambient temperature for 2 h and then heated at 90° C. for 2.5 days. The solvent was removed in vacuo and the residue was suspended in methanol. The methanol suspension was heated and filtered. The yellow solid was washed with 1M aqueous hydrochloric acid solution, water and methanol then dried under vacuum to give 3.17 g (82% yield) of the title compound, m.p. >250° C.

$^1$H NMR (CDCl$_3$) δ7.85 (dd, 1H, H$_5$), 3.85–3.9 (m, 4H, morpholine), 3.78 (m, 1H, NCH), 3.42 (br s, 4H, morpholine), 1.13–1.36 (m, 4H, cyclopropyl).

EXAMPLES 2–18

Following the synthesis outlined in Example 1, starting with 2,3,4,5-tetrafluorobenzoic acid and substituting morpholine with the appropriate amine in Step 5, and substituting phenyl N-cyclopropyliminochlorothioformate with phenyl N-ethyliminochlorothioformate (prepared by the procedure described in Step 1 of Example 1, substituting cyclopropylamine with ethylamine) when appropriate in Step 2, Examples 2–18 were made (as the free base unless otherwise noted) as disclosed in Table 1. The structure of each was confirmed by melting point and NMR spectroscopy as designated.

TABLE 1

Examples 2-18

| Example No. | Structure | Amine | m.p. | ¹H NMR signal* |
|---|---|---|---|---|
| 2 | (isothiazolo-quinolone with cyclopropyl, 6,8-difluoro, 7-piperazinyl; MeSO₃H salt) | piperazine (HN-NH) | >250° C. | 8.11 |
| 3 | (isothiazolo-quinolone with cyclopropyl, 6,8-difluoro, 7-(2-methylpiperazinyl)) | 2-methylpiperazine | >250° C. | 8.02 |
| 4 | (isothiazolo-quinolone with cyclopropyl, 6,8-difluoro, 7-(4-methylpiperazinyl)) | 4-methylpiperazine (Me-N-NH) | >250° C. | 8.02 |
| 5 | (isothiazolo-quinolone with cyclopropyl, 6,8-difluoro, 7-[4-(2-hydroxyethyl)piperazinyl]; HCl salt) | 1-(2-hydroxyethyl)piperazine | >250° C. | 8.04 |

TABLE 1-continued

Examples 2–18

| Example No. | Structure | Amine | m.p. | ¹H NMR signal* |
|---|---|---|---|---|
| 6 | (isothiazolo-quinolone with cyclopropyl, two F, and thiomorpholinyl substituent) | thiomorpholine (H-N with S) | >250° C. | 7.86 (CDCl₃) |
| 7 | (isothiazolo-quinolone with cyclopropyl, two F, and octahydroazocinyl substituent) | hexamethyleneimine / homopiperazine (8-membered N-H ring) | >250° C. | 8.03 |
| 8 | (isothiazolo-quinolone with cyclopropyl, two F, and piperidinyl substituent) | piperidine | >250° C. | 8.32 |
| 9 | (isothiazolo-quinolone with cyclopropyl, two F, and 3-hydroxypiperidinyl substituent) | 3-hydroxypiperidine | >250° C. | 8.03 |

TABLE 1-continued

Examples 2-18

| Example No. | Structure | Amine | m.p. | ¹H NMR signal* |
|---|---|---|---|---|
| 10 | (isothiazoloquinolone with cyclopropyl, 2F, and 4-hydroxypiperidinyl substituent) | 4-hydroxypiperidine | >250° C. | 8.20 |
| 11 | (isothiazoloquinolone with cyclopropyl, 2F, and 3-aminopyrrolidinyl substituent; MeSO₃H) | 3-aminopyrrolidine ** | >250° C. | 7.98 |
| 12 | (isothiazoloquinolone with cyclopropyl, 2F, and 3-(aminomethyl)pyrrolidinyl substituent; MeSO₃H) | 3-(aminomethyl)pyrrolidine | >250° C. | 7.94 |
| 13 | (quinolone with cyclopropyl, 2F, and 1-benzyl-4-aminopiperidinyl substituent) | 1-benzyl-4-aminopiperidine | >250° C. | 8.11 |

TABLE 1-continued

Examples 2-18

| Example No. | Structure | Amine | m.p. | ¹H NMR signal* |
|---|---|---|---|---|
| 14 | (isothiazoloquinolone with 4-(piperazin-1-yl)-3,5-difluorophenyl; MeSO₃H salt) | piperazine (NH–CH₂CH₂–NH) | >250° C. | 7.82 (d₆-DMSO) |
| 15 | (isothiazoloquinolone with 4-(3-methylpiperazin-1-yl)-3,5-difluorophenyl; MeSO₃H salt) | 2-methylpiperazine | >250° C. | 7.71 |
| 16 | (isothiazoloquinolone with 4-(4-methylpiperazin-1-yl)-3,5-difluorophenyl; MeSO₃H salt) | N-methylpiperazine | >250° C. | 7.81 (d₆-DMSO) |
| 17 | (isothiazoloquinolone with 4-(3-aminopyrrolidin-1-yl)-3,5-difluorophenyl; MeSO₃H salt) | 3-aminopyrrolidine | >250° C. | 7.71 (d₆-DMSO) |

TABLE 1-continued
Examples 2-18

| Example No. | Structure | Amine | m.p. | ¹H NMR signal* |
|---|---|---|---|---|
| 18 | (structure shown: benzoyl-isothiazolone with F, F, pyrrolidinyl-NH2, N-ethyl, CF₃COOH) | (3-aminomethyl pyrrolidine, NH) | >250° C. | |

*δ (ppm) for H₅ in 50/50 trifluoroacetic acid (TFA)/deuterio-acetic acid (CD₃COOD) unless a different solvent is noted.
**prepared by hydrolysis of the corresponding NNCOOC(CH₃)₃ derivative

EXAMPLE 19

9-Cyclopropyl-6-fluoro-7-(1-piperazinyl)-2,3,4,9-tetrahydroisothiazolo[5,4-b]quinoline-3,4-dione

Step 1: Ethyl 3-cyclopropylamino-3-methylthio-2-(2',4',5'-trifluoro)benzoylacrylate Sodium hydride (1.3 g of Aldrich 60% NaH in mineral oil) was added slowly to a solution of 7.6 g (30.9 mmol) of ethyl 2,4,5-trifluorobenzoyl acetate (prepared as described by D. T. Chu in U.S. Pat. No. 4,767,762—Example 1a) and 3.38 g (34.1 mmol) of N-cyclopropylthioisocyanate (prepared as described in Example 1a of this application) in 50 mL of N,N-dimethylformamide (DMF), cooled in an ice bath. After the addition of NaH was complete, the reaction mixture was allowed to warm to ambient temperature and stirred at ambient temperature for 22.5 h. Methyl iodide (2.1 mL, 33.7 mmol) was added to the reaction mixture at ambient temperature and the resultant solution was stirred at ambient temperature for 17 h. Glacial acetic acid (1 mL) was added and the solvent was removed in vacuo. The residue was dissolved in methylene chloride and the methylene chloride solution was washed with brine, dried over anhydrous magnesium sulfate, filtered and concentrated under reduced pressure. The residue was purified by column chromatography on silica gel eluted with 1.5% ethyl acetate in methylene chloride to give 7 g (64% yield) of the title compound.

Step 2: 1-Cyclopropyl-6,7-difluoro-3-ethoxycarbonyl-2-methylthioquinoline-4-one To a solution of 4.23 g (11.8 mmol) of ethyl 3-cyclopropylamino-3-methylthio-2-(2',4',5'-trifluoro)benzoylacrylate, from Step 1, in 40 mL of THF, was added 480 mg of 60% sodium hydride in mineral oil. The reaction mixture was heated at 60° C. for 24 h and then 0.5 mL of glacial acetic acid was added. The solvents were removed in vacuo and the residue dissolved in chloroform. The chloroform solution was washed with water, dried over anhydrous magnesium sulfate and concentrated in vacuo. The residue was crystallized from diethyl ether to give 2.49 (62.5% yield) of the title compound, m.p. 137.5° C. Analysis calculated for $C_{16}H_{15}F_2NO_3S + \frac{1}{4}H_2O$: C, 55.17; H, 4.59; N, 4.02. Found: C, 55.41; H, 4.51; N, 3.89.

Step 3: 1-Cyclopropyl-6,7-difluoro-3-ethoxycarbonyl-2-methylsulfinylquinoline-4-one To a solution of 2.225 g (6.56 mmol) of 1-cyclopropyl-6,7-difluoro-3-ethoxycarbonyl-2-methylthioquinoline-4-one, from Step 2, in 70 mL of methylene chloride, was added 1.486 g (6.97 mmol) of 3-chloroperoxybenzoic acid (Aldrich 80%). After being stirred at ambient temperature for 4 h, the reaction mixture was diluted with methylene chloride and washed with cold dilute aqueous sodium bicarbonate solution. The organic layer was dried over anhydrous magnesium sulfate and concentrated in vacuo. The residue was crystallized from diethyl ether to give 2.09 g (89.75% yield) of the title compound, m.p. 207° C. Analysis calculated for $C_{16}H_{15}F_2NO_4S + \frac{1}{4}H_2O$: C, 53.41; H, 4.31; N, 3.89. Found: C, 53.49; H, 4.34; N, 3.75.

Step 4: 9-Cyclopropyl-6,7-difluoro-2,3,4,9-tetrahydroisothiazolo[5,4-b]quinoline-3,4-dione To a solution of 4 g (11.268 mmol) of 1-cyclopropyl-6,7-difluoro-3-ethoxycarbonyl-2-methylsulfinylquinoline-4-one, from Step 3, in 200 mL of THF, was added 14 mL of 1N sodium hydrosulfide solution in THF. After being stirred at ambient temperature for 4 h, the reaction mixture was evaporated in vacuo. The residue was dissolved in water and the insoluble material removed by filtration. To the aqueous filtrate was added 20 mL of 1N hydrochloric acid solution and the resultant solution was extracted with methylene chloride. The methylene chloride was evaporated under reduced pressure to yield 3.1 g of crude 1-cyclopropyl-6,7-difluoro-3-ethoxycarbonyl-2-mercaptoquinoline-4-one which was dissolved in 85 mL of THF. To the THF solution was added 7.2 g of solid sodium bicarbonate and 128 mL of water, followed by the addition of 3.77 g hydroxylamine-O-sulfonic acid. After being stirred at ambient temperature for 3 h, the reaction mixture was diluted with water and filtered. The solid filter cake was suspended in boiling methanol and the suspension was cooled and filtered to give 2.4 g (72.4% yield from 1-cyclopropyl-6,7-difluoro-3-ethoxycarbonyl-2-methylsulfinylquinoline-4-one) of the title compound, m.p. >250° C. An additional 200 mg of title compound was obtained from the aqueous filtrate upon acidification with 85 mL of 1N hydrochloric acid solution and filtration. Analysis calculated for $C_{13}H_8F_2N_2O_2S + \frac{1}{2}H_2O$: C, 51.49; H, 2.97; N, 9.24. Found: C, 51.46; H, 2.70; N, 9.20.

Step 5: 9-Cyclopropyl-6-fluoro-7-(1-piperazinyl)-2,3,4,9-tetrahydroisothiazolo[5,4-b]quinoline-3,4-dione To a suspension of 436 mg (1.48 mmol) of 9-cyclopropyl-6,7-difluoro-2,3,4,9-tetrahydroisothiazolo[5,4-b]quinoline-3,4-dione, from Step 4, in 9mL of pyridine at 70° C., was added 755 mg (8.78 mmol) of piperazine. A clear colorless solution was formed. After being stirred for 2 days at 70° C., the reaction mixture was cooled to ambient temperature and filtered. The solid was washed with diethyl ether and cold water to give 480 mg (91% yield) of the title compound, m.p. >275° C. Analysis calculated for $C_{17}H_{17}FN_4O_2S$: C, 55.97; H, 4.83; N, 14.94. Found: C, 55.84; H, 4.83; N, 15.36.

EXAMPLES 20-27

Following the synthesis outlined in Example 19, substituting piperazine with the appropriate amine, and N-cyclopropyl thioisocyanate with N-ethyl thioisocyanate (prepared by the procedure described in Step 1 of Example 1, substituting cyclopropylamine with ethylamine) when appropriate, Examples 20-27 were made (as the free base, unless otherwise noted) as disclosed in Table 2. The structure of each was confirmed by melting point and NMR spectroscopy as designated.

TABLE 2

Examples 20-27

| Example No. | R | Y | m.p. | ¹H NMR signal* H-5 | H-8 |
|---|---|---|---|---|---|
| 20 | 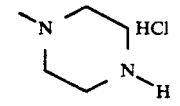 |  | >250° C. | 7.56 (CD₃COOD) | 7.91 |
| 21 | 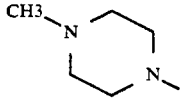 |  | >250° C. | 7.51 (CD₃COOD) | 7.88 |
| 22 | 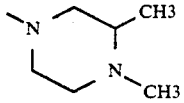 |  | >250° C. | 7.86 | 8.22 |
| 23 | 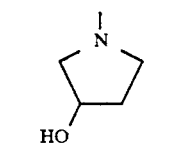 |  | >250° C. | 6.93 (d₆-DMSO) | 7.78 |
| 24 | 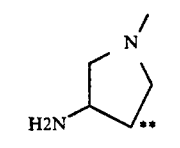 |  | >250° C. | 7.32 | 8.03 |
| 25 | 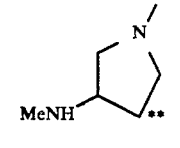 | 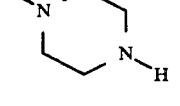 | >250° C. | 7.33 | 8.07 |
| 26 | Et | 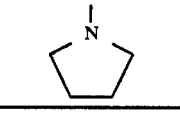 | >250° C. | 6.97 (d₆-DMSO) | 7.81 |
| 27 | Et |  | >250° C. | 6.79 | 8.06 |

*δ (ppm) for H₅ and H₈ in 50/50 trifluoroacetic acid (TFA)/deuterio-acetic acid (CD₃COOD) unless a different solvent is noted.
**prepared by hydrolysis of the corresponding NHCOOC(CH₃)₃ derivative

EXAMPLE 28

11-Ethyl-2,3,4,11-tetrahydroisothiazolo[5,4-b]quinoline-3,4-dione

Step 1: Ethyl N-ethyl-N-(1-naphthyl)-2-ethoxycarbonyl-3-mercaptoacrylate

A solution of 0.42 g (2.45 mmol) of N-ethyl naphthylamine (commercially available from Aldrich Chemical Company) and 0.5 g (1.34 mmol) of 2,4-bis(bis(ethoxycarbonyl)methylene)-1,3-dithiatane (prepared as described by M. S. Raash in *J. Org Chem*, 35, 3470-83 (1970)) in 15 mL of toluene containing 0.72 mL of diazabicycloundecane (DBU) was heated at reflux temperature for 4-5 h. The reaction mixture was cooled to ambient temperature and the unreacted starting material was removed by filtration and rinsed with diethyl ether. The filtrate was washed with 3×20 mL of 5% aqueous hydrochloric acid solution, 2×20 mL of water and brine, dried over anhydrous sodium sulfate, filtered and concentrated under reduced pressure to give an oil. The oil was purified on silica gel eluted with diethyl ether/hexanes (1:1, v/v) to give 0.235 g (47% yield) of ethyl N-ethyl-N-(1-naphthyl)-2-ethoxycarbonyl-3-mercaptoacrylate.

Step 2: 4,11-Dihydro-3-ethoxycarbonyl-11-ethyl-2-mercaptobenzo[h]quinoline-4-one Ethyl N-ethyl-N-(1-naphthyl)-2-ethoxycarbonyl-3-mercaptoacrylate (0.3 g, 0.80 mmol) from Step 1 was combined with 4 mL of polyphosphoric acid and the mixture was heated to 100° C. for 2 h. After cooling the reaction mixture to ambient temperature, ice was added and the resultant mixture extracted with 2×25 mL of methylene chloride. The combined methylene chloride extract was washed with water, dried over anhydrous sodium sulfate, filtered and concentrated under reduced pressure to afford 0.1 g (38% yield) of the title compound.

Step 3: 11-Ethyl-2,3,4,11-tetrahydroisothiazolo[5,4-b]-benzo[h]quinoline-3,4-dione The procedures described in Steps 3 and 4 of Example 1 were repeated, replacing 1-cyclopropyl-1,4-dihydro-3-ethoxycarbonyl-2-phenylthio-6,7,8-trifluoroquinoline-4-one with 0.1 g (0.3 mmol) of 4,11-dihydro-3-ethoxycarbonyl-11-ethyl-2-mercaptobenzo[h]quinoline-4-one from Step 2 above to afford 55 mg (62% yield) of the title compound, m.p.>250° C.; ¹H NMR (50/50 CF₃COOD/CD₃COOD) d 8.5 (d, 1H, H₅).

EXAMPLE 29

9-Ethyl-6,7-methylenedioxy-2,3,4,9-tetrahydroisothiazolo[5,4-b]quinoline-3,4-dione The procedure described in Example 28 was repeated replacing N-ethyl naphthylamine with N-ethyl-3,4-methylenedioxy-aniline to afford the title compound, ¹H NMR (50/50 CF₃COOD/CD₃COOD) d 7.83 (d, 1H, H₅).

EXAMPLE 30

9-Ethyl-7-phenoxy-2,3,4,9-tetrahydroisothiazolo[5,4-b]quinoline-3,4-dione

The procedure described in Example 28 was repeated replacing N-ethyl naphthylamine with N-ethyl-3-phenoxyaniline to afford the title compound.

EXAMPLES 31-159

Following the procedures described in Example 1, starting with 2,3,4,5-tetrafluorobenzoic acid and using the appropriate iminochlorothioformate, N-phenylisothiocyanate or N-(4-pyridyl)isothiocyanate in Step 2 and the appropriate amine in Step 5, Examples 31-159 are prepared as disclosed in Table 3. The N-methylamino compounds are prepared from hydrolysis of the N-(N'-methyl-N'-formylamino) compound by hydrolysis with dilute hydrochloric acid.

TABLE 3

Examples 31-159

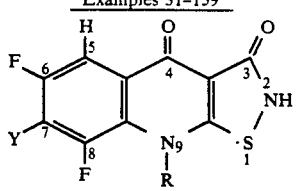

| Example No. | R | Y |
|---|---|---|
| 31 | cyclopropyl | -N(piperazinyl)N-Me, Me |
| 32 | cyclopropyl | -N-pyrrolidinyl |
| 33 | cyclopropyl | -N-pyrrolidinyl-NH2, Me |
| 34 | cyclopropyl | -N-pyrrolidinyl-NHEt |
| 35 | cyclopropyl | -N-pyrrolidinyl-NH2, Cl |
| 36 | cyclopropyl | -NH-benzyl |
| 37 | cyclopropyl | -NH-quinuclidinyl |
| 38 | cyclopropyl | -N(Me)CH2CH2N(Me)Me |
| 39 | Et | -N(piperazinyl)-CH2CH2OH |
| 40 | Et | -N(thiomorpholinyl)S |
| 41 | Et | -N-morpholinyl |
| 42 | Et | -N(homopiperazinyl)NH |
| 43 | Et | -N-piperidinyl |
| 44 | Et | -N-piperidinyl-OH (3-OH) |
| 45 | Et | -N-piperidinyl-OH (4-OH) |
| 46 | Et | -N(piperazinyl)N-Me, Me |
| 47 | Et | -N-pyrrolidinyl |

TABLE 3-continued

Examples 31–159

[Structure: fluorinated isothiazoloquinolinone core with positions labeled H5, F6, Y7, F8, N9-R, and ring atoms 1(S), 2(NH), 3(C=O), 4(C=O)]

| Example No. | R | Y |
|---|---|---|
| 48 | Et | 1-methyl-3-amino-4-methylpyrrolidinyl |
| 49 | Et | (1-methylpyrrolidin-3-yl)methyl-NHEt |
| 50 | Et | 1-methyl-4-chloro-3-(aminomethyl)pyrrolidinyl |
| 51 | Et | –NH–CH₂–phenyl (benzylamino) |
| 52 | Et | –NH–quinuclidinyl |
| 53 | Et | –NH–(1-benzylpiperidin-4-yl) |
| 54 | Et | Me₂N–CH₂CH₂–N(Me)– (with extra Me) |
| 55 | 4-F-phenyl | piperazin-1-yl (NH) |
| 56 | 4-F-phenyl | 3-methylpiperazin-1-yl |
| 57 | 4-F-phenyl | 4-methylpiperazin-1-yl |
| 58 | 4-F-phenyl | 4-(2-hydroxyethyl)piperazin-1-yl |
| 59 | 4-F-phenyl | thiomorpholin-4-yl |
| 60 | 4-F-phenyl | morpholin-4-yl |
| 61 | 4-F-phenyl | 1,4-diazepan-1-yl (NH) |
| 62 | 4-F-phenyl | piperidin-1-yl |
| 63 | 4-F-phenyl | 3-hydroxypiperidin-1-yl |
| 64 | 4-F-phenyl | 4-hydroxypiperidin-1-yl |
| 65 | 4-F-phenyl | 1-methyl-3-aminopyrrolidinyl |
| 66 | 4-F-phenyl | 1-methyl-3-(aminomethyl)pyrrolidinyl |
| 67 | 4-F-phenyl | –NH–(1-benzylpiperidin-4-yl) |

TABLE 3-continued

Examples 31-159

| Example No. | R | Y |
|---|---|---|
| 68 | 4-F-phenyl | -N(piperazinyl)-N-Me with Me substituent |
| 69 | 4-F-phenyl | pyrrolidinyl-N- |
| 70 | 4-F-phenyl | N-methylpyrrolidine with NH2 and Me substituents |
| 71 | 4-F-phenyl | N-methylpyrrolidine with CH2NHEt |
| 72 | 4-F-phenyl | N-methylpyrrolidine with CH2NH2 and Cl |
| 73 | 4-F-phenyl | -NH-CH2-phenyl |
| 74 | 4-F-phenyl | -NH-quinuclidinyl |
| 75 | 4-F-phenyl | Me2N-CH2CH2-N(Me)- with additional Me |
| 76 | 2,4-diF-phenyl | -N(piperazinyl)NH |
| 77 | 2,4-diF-phenyl | -N(piperazinyl)NH with Me |
| 78 | 2,4-diF-phenyl | -N(piperazinyl)-N-Me |
| 79 | 2,4-diF-phenyl | -N(piperazinyl)-N-CH2CH2OH |
| 80 | 2,4-diF-phenyl | -N(thiomorpholinyl) |
| 81 | 2,4-diF-phenyl | -N(morpholinyl) |
| 82 | 2,4-diF-phenyl | -N(homopiperazinyl)-NH |
| 83 | 2,4-diF-phenyl | -N(piperidinyl) |
| 84 | 2,4-diF-phenyl | -N(piperidinyl)-3-OH |
| 85 | 2,4-diF-phenyl | -N(piperidinyl)-4-OH |
| 86 | 2,4-diF-phenyl | N-methylpyrrolidine-3-NH2 |

TABLE 3-continued

Examples 31-159

[Structure: Fluoroquinolone-type core with positions labeled H-5, F-6, Y-7, F-8, N-9-R, S-1, 2-NH, 3-C(O), 4-C(O)]

| Example No. | R | Y |
|---|---|---|
| 87 | 2,4-difluorophenyl | 1-methylpyrrolidin-3-yl-CH2NH2 |
| 88 | 2,4-difluorophenyl | -NH-(1-benzylpiperidin-4-yl) |
| 89 | 2,4-difluorophenyl | 3-methyl-4-methylpiperazin-1-yl |
| 90 | 2,4-difluorophenyl | 1-methylpyrrolidin-1-yl |
| 91 | 2,4-difluorophenyl | 1-methyl-4-methyl-3-aminopyrrolidinyl |
| 92 | 2,4-difluorophenyl | 1-methylpyrrolidin-3-yl-CH2NHEt |
| 93 | 2,4-difluorophenyl | 1-methyl-4-chloro-3-(aminomethyl)pyrrolidinyl |
| 94 | 2,4-difluorophenyl | -NH-CH2-phenyl |
| 95 | 2,4-difluorophenyl | -NH-(quinuclidin-4-yl) |
| 96 | 2,4-difluorophenyl | -N(Me)-CH2CH2-N(Me)2 (with extra Me) |
| 97 | pyridin-4-yl | piperazin-1-yl |
| 98 | pyridin-4-yl | 3-methylpiperazin-1-yl |
| 99 | pyridin-4-yl | 4-methylpiperazin-1-yl |
| 100 | pyridin-4-yl | 4-(2-hydroxyethyl)piperazin-1-yl |
| 101 | pyridin-4-yl | thiomorpholin-4-yl |
| 102 | pyridin-4-yl | morpholin-4-yl |
| 103 | pyridin-4-yl | 1-methyl-1,4-diazepan-4-yl |
| 104 | pyridin-4-yl | piperidin-1-yl |

TABLE 3-continued

Examples 31-159

| Example No. | R | Y |
|---|---|---|
| 105 | 4-pyridyl | 1-methylpiperidin-3-ol (N-linked, 3-OH) |
| 106 | 4-pyridyl | 1-methylpiperidin-4-ol (N-linked, 4-OH) |
| 107 | 4-pyridyl | 1-methyl-3-aminopyrrolidine |
| 108 | 4-pyridyl | 1-methyl-3-(aminomethyl)pyrrolidine |
| 109 | 4-pyridyl | —NH—(1-benzylpiperidin-4-yl) |
| 110 | 4-pyridyl | 4-methyl-3-methyl-piperazin-1-yl |
| 111 | 4-pyridyl | 1-methylpyrrolidin-3-yl (N-linked) |
| 112 | 4-pyridyl | 1-methyl-4-methyl-3-aminopyrrolidine |
| 113 | 4-pyridyl | 1-methyl-3-(CH2NHEt)pyrrolidine |
| 114 | 4-pyridyl | 1-methyl-3-(aminomethyl)-4-chloropyrrolidine |
| 115 | 4-pyridyl | —NH—CH2—Ph (N-methyl benzyl amine) |
| 116 | 4-pyridyl | —NH-quinuclidinyl |
| 117 | 4-pyridyl | —N(Me)CH2CH2N(Me)2 |
| 118 | CH2CH2F | piperazin-1-yl (NH) |
| 119 | CH2CH2F | piperazin-1-yl (NH) |
| 120 | CH2CH2F | 4-methylpiperazin-1-yl |
| 121 | CH2CH2F | 4-(2-hydroxyethyl)piperazin-1-yl |
| 122 | CH2CH2F | thiomorpholin-4-yl |
| 123 | CH2CH2F | morpholin-4-yl |

TABLE 3-continued

Examples 31-159

| Example No. | R | Y |
|---|---|---|
| 124 | ~~~F (propyl-F) | 1-methyl-1,4-diazepane (N-Me, NH) |
| 125 | ~~~F | piperidin-1-yl |
| 126 | ~~~F | 3-hydroxypiperidin-1-yl |
| 127 | ~~~F | 4-hydroxypiperidin-1-yl |
| 128 | ~~~F | 3-amino-1-methylpyrrolidin-1-yl |
| 129 | ~~~F | 3-(aminomethyl)-1-methylpyrrolidin-1-yl |
| 130 | ~~~F | —NH-(1-benzylpiperidin-4-yl) |
| 131 | ~~~F | 4-methyl-3-methylpiperazin-1-yl (—N, N—Me, Me) |
| 132 | ~~~F | pyrrolidin-1-yl |
| 133 | ~~~F | 3-amino-4-methyl-1-methylpyrrolidin-1-yl |
| 134 | ~~~F | 3-((ethylamino)methyl)-1-methylpyrrolidin-1-yl |
| 135 | ~~~F | 3-(aminomethyl)-4-chloro-1-methylpyrrolidin-1-yl |
| 136 | ~~~F | —NH—CH2—C6H5 (N-methylbenzylamino) |
| 137 | ~~~F | —NH-(quinuclidin-4-yl) |
| 138 | ~~~F | Me2N—CH2CH2—N(Me)— |
| 139 | —NHMe | piperazin-1-yl |
| 140 | —NHMe | 3-methylpiperazin-1-yl |
| 141 | —NHMe | 4-methylpiperazin-1-yl |
| 142 | —NHMe | 4-(2-hydroxyethyl)piperazin-1-yl |

TABLE 3-continued

Examples 31-159

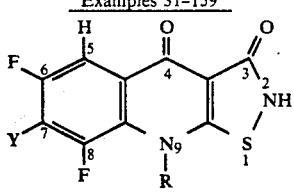

| Example No. | R | Y |
|---|---|---|
| 143 | —NHMe | 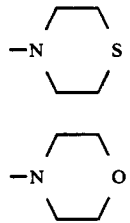 |
| 144 | —NHMe | 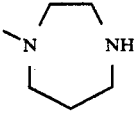 |
| 145 | —NHMe |  |
| 146 | —NHMe | 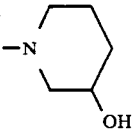 |
| 147 | —NHMe | 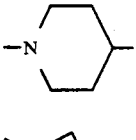 |
| 148 | —NHMe |  |
| 149 | —NHMe |  |
| 150 | —NHMe | 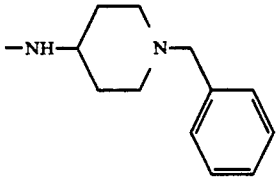 |
| 151 | —NHMe | 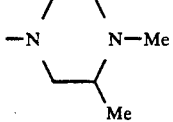 |
| 152 | —NHMe | 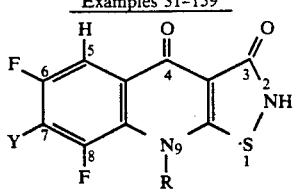 |
| 153 | —NHMe | 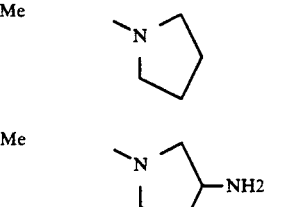 |
| 154 | —NHMe | 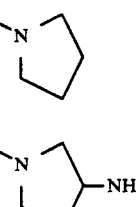 |
| 155 | —NHMe | 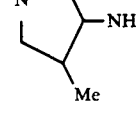 |
| 156 | —NHMe | 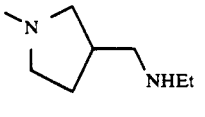 |
| 157 | —NHMe | 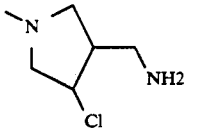 |
| 158 | —NHMe | 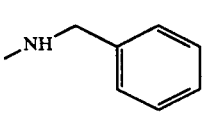 |
| 159 | —NHMe | 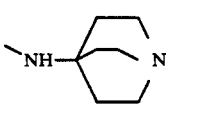 |

EXAMPLES 160-197

Following the procedures described in Example 1, starting with 3-chloro-2,4,5-trifluorobenzoic acid and using the appropriate iminochlorothioformate in Step 2 and the appropriate amine in Step 5, Examples 160-197 are prepared as disclosed in Table 4.

TABLE 4
Examples 160–197
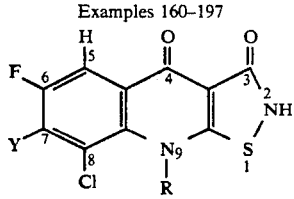
| Example No. | R | Y |
|---|---|---|
| 160 |  | |
| 161 |  | |
| 162 | 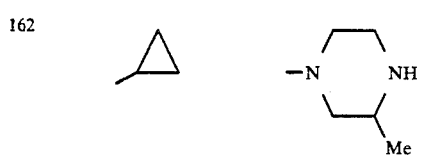 | |
| 163 |  | |
| 164 | 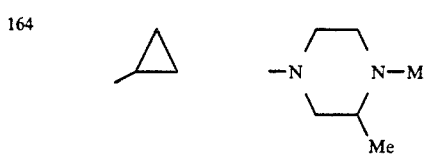 | |
| 165 | 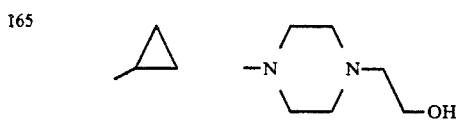 | |
| 166 |  | |
| 167 |  | |
| 168 |  | |
| 169 | 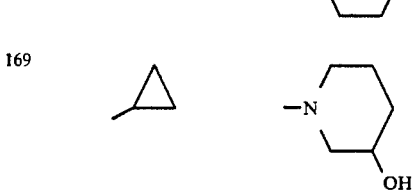 | |
TABLE 4-continued
Examples 160–197
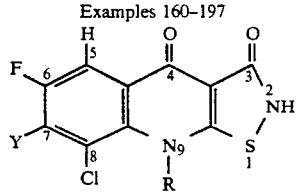
| Example No. | R | Y |
|---|---|---|
| 170 | 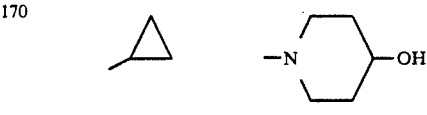 | |
| 171 |  | |
| 172 | 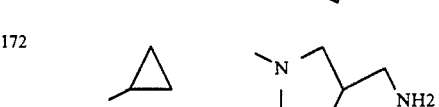 | |
| 173 | 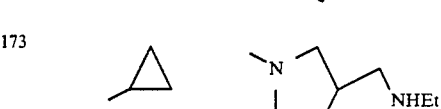 | |
| 174 |  | |
| 175 |  | |
| 176 |  | |
| 177 |  | |
| 178 | 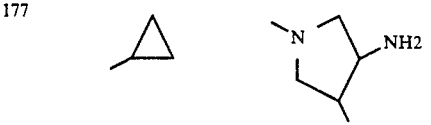 | |
| 179 | Et | 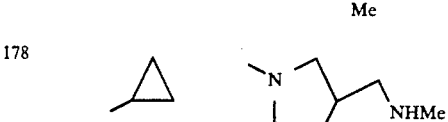 |
| 180 | Et |  |

TABLE 4-continued

Examples 160-197

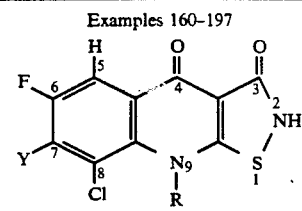

| Example No. | R | Y |
|---|---|---|
| 181 | Et | —N(piperazine)NH, Me-substituted |
| 182 | Et | —N(piperazine)N—Me |
| 183 | Et | —N(piperazine)N—Me, Me-substituted |
| 184 | Et | —N(piperazine)N—CH2CH2OH |
| 185 | Et | —N(thiomorpholine)S |
| 186 | Et | —N(homopiperazine)NH |
| 187 | Et | —N(piperidine) |
| 188 | Et | —N(piperidine)-3-OH |
| 189 | Et | —N(piperidine)-4-OH |
| 190 | Et | N-Me-pyrrolidine-3-NH2 |
| 191 | Et | N-Me-pyrrolidine-3-CH2NH2 |
| 192 | Et | N-Me-pyrrolidine-3-CH2NHEt |
| 193 | Et | N-Me-pyrrolidine |
| 194 | Et | N-Me-pyrrolidine-3-OH |
| 195 | Et | N-Me-pyrrolidine-3-CH2NH2, 4-Cl |
| 196 | Et | N-Me-pyrrolidine-3-NH2, 4-Me |
| 197 | Et | N-Me-pyrrolidine-3-CH2NHMe |

EXAMPLES 198-227

Following the procedures described in Example 19, starting with 2,4,5-trifluorobenzoic acid and using the appropriate thioisocyanate in Step 1 and the appropriate amine in Step 5, Examples 198-227 are synthesized as disclosed in Table 5.

TABLE 5
Examples 198-227
| Example No. | R | Y |
|---|---|---|
| 198 | 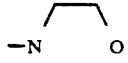 |  |
| 199 | 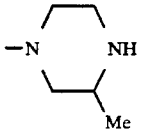 |  |
| 200 | 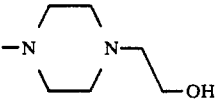 |  |
| 201 | 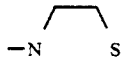 |  |
| 202 | 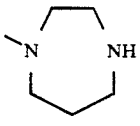 |  |
| 203 | 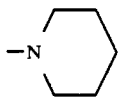 |  |
| 204 | 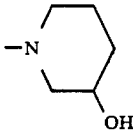 |  |
| 205 | 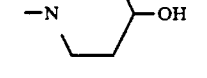 |  |
| 206 | 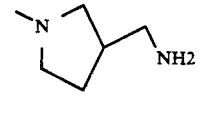 |  |
| 207 | 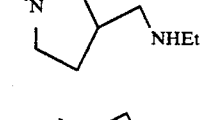 |  |
| 208 | 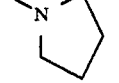 | 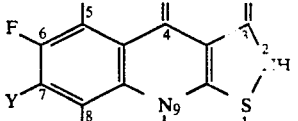 |
TABLE 5-continued
Examples 198-227
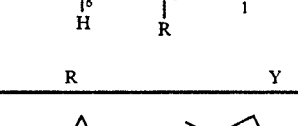
| Example No. | R | Y |
|---|---|---|
| 209 | 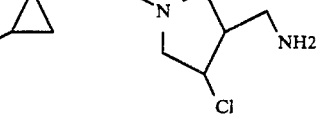 | 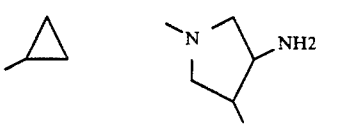 |
| 210 | 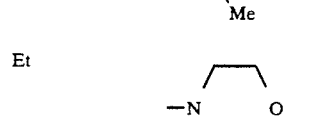 | 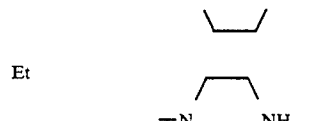 |
| 211 | Et | 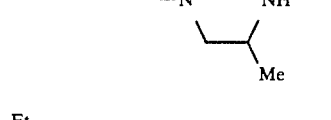 |
| 212 | Et | 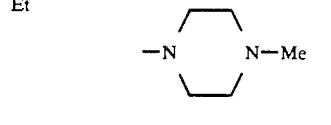 |
| 213 | Et | 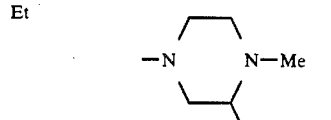 |
| 214 | Et | 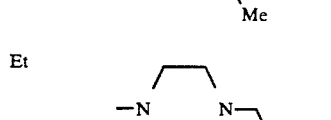 |
| 215 | Et | 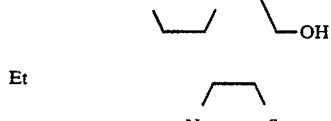 |
| 216 | Et | 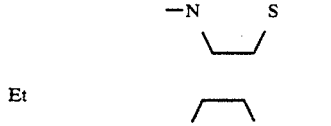 |
| 217 | Et | 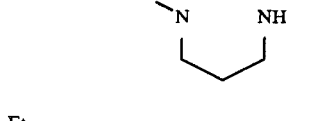 |
| 218 | Et | 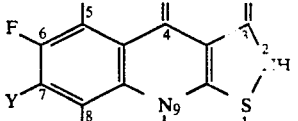 |

TABLE 5-continued

Examples 198-227

[Structure: tetrahydroisothiazolo[5,4-b]quinoline-3,4-dione core with positions labeled F-6, Y-7, H-8, N9-R, H-5, O-4, O-3, NH-2, S-1]

| Example No. | R | Y |
|---|---|---|
| 219 | Et | —N⟨piperidine⟩—OH (3-hydroxy) |
| 220 | Et | —N⟨piperidine⟩—OH (4-hydroxy) |
| 221 | Et | —N⟨pyrrolidine⟩—NH2 |
| 222 | Et | —N⟨pyrrolidine⟩—CH2NH2 |
| 223 | Et | —N⟨pyrrolidine⟩—CH2NHEt |
| 224 | Et | —N⟨pyrrolidine⟩—OH |
| 225 | Et | —N⟨pyrrolidine⟩—CH(Cl)—NH2 |
| 226 | Et | —N⟨pyrrolidine⟩—NH2 with Me |
| 227 | Et | —N⟨pyrrolidine⟩—NHMe |

EXAMPLE 228

9-Cyclopropyl-6,8-difluoro-7-(3'-(N-norvalyl)amino-pyrrolidinyl)-2,3,4,9-tetrahydroisothiazolo[5,4-b]quinoline-3,4-dione 3-Amino-1-benzylpyrrolidine (I. Sumio and T. Matsuo, Japanese Kokai JP 5328161, published Mar. 16, 1978) was coupled to N-t-butoxycarbonyl norvaline (Boc-nVal) using conventional N-hydroxysuccinimide coupling procedures. The 1-benzyl group was removed by hydrogenolysis in methanol using palladium on carbon catalyst. The 3-(N-Boc-norvalyl)aminopyrrolidine was then reacted with 9-cyclopropyl-6,7,8-trifluoro-2,3,4,9-tetrahydroisothiazolo[5,4-b]quinoline-3,4-dione, the product of Step 4 of Example 1, as described in Step 5 of Example 1, replacing morpholine with 3-(N-Boc-norvalyl)aminopyrrolidine, to give 9-cyclopropyl-6,8-difluoro-7-(3'-(N-norvalyl)amino-pyrrolidinyl)-2,3,4,9-tetrahydroisothiazolo[5,4-b]quinoline-3,4-dione with the nitrogen of the amino acid protected with a Boc group. The Boc protecting group was removed by standard hydrolysis using trifluoroacetic acid and dilute aqueous hydrochloric acid.

The condensation of amino groups (such as those present in the certain of the compounds of this invention) with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxy-benzotriazole) method and the like. Classical methods for amino acid condensation reactions are described in "Peptide Synthesis" Second Edition, M. Bodansky, Y. S. Klausner and M. A. Ondetti (1976). It is contemplated that the amino acid coupling reaction could be carried out before or after the amino-containing group is incorporated into the compound by displacement of the 7-fluorine atom of the appropriate intermediate.

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Z), o-chlorobenzyloxycarbonyl((2-Cl)Z), p-nitrobenzyloxycarbonyl (Z(NO$_2$)), p-methoxybenzyloxycarbonyl (Z(OMe)), t-butoxycarbonyl (Boc), t-amyloxycarbonyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfenyl (Nps), diphenylphosphinothioyl (Ppt) and dimethylphosphinothioyl (Mpt).

The examples of protecting groups for carboxyl groups involve, for example, benzyl ester (OBzl), cyclohexyl ester, 4-nitrobenzyl ester (OBzINO$_2$), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (N$^G$) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mts) and the like, and the thiol group in cysteine may be protected with benzyl, p-methoxybenzyl, triphenylmethyl, acetomidomethyl, ethylcarbamyl, 4-methylbenzyl (4-MeBzl), 2,4,6-trimethylbenzyl (Tmb) and the like, and the hydroxy group in serine may be protected with benzyl (Bzl), t-butyl, acetyl, tetrahydropyranyl (THP) and the like.

Using the procedure outlined in Example 228, or any of the other conventional condensation methods listed above, other amino acid derivatives of the compounds of this invention having an amino group can be prepared. Examples of amino acids which can be coupled, either alone or in combination with one and other, include naturally occurring amino acids such as glycine, alanine, leucine, isoleucine, methionine, phenylalanine, valine, and the like, as well as synthetic amino acids such as cyclohexylalanine, cyclohexylglycine, aminopentanoic acid, and the like.

Antitumor Activity

It has been found that the compounds of the present invention possess inhibitory activity against a key cellular enzyme, topoisomerase II and cause related topoisomerase II-mediated DNA breakage in cell free assays, an activity which has been correlated with cytotoxicity. These compounds exhibit cytotoxic activity in vitro against a variety of cultured tumor and leukemia cell lines and and in vivo in mouse tumor and leukemia models.

Antitumor activity was assayed using the DNA Breakage Assay described below.

DNA Breakage Assay

The DNA breakage assay requires two major reagents: DNA topoisomerase II and radiolabeled DNA. DNA topoisomerase II (topo II) was isolated from calf thymus as described by B. D. Holligan, et al. in *J. Biol. Chem.*, 260, 2475-2482 (1985). Pure enzyme or partially purified extracts enriched in topo II activity may be used. PBR 322 plasmid was used as the DNA substrate. This plasmid, which is isolated in the closed circular form, is first linearized using, a restriction enzyme which cuts the plasmid in only one place. The newly exposed ends of the plasmid are then labeled with the radionuclide, 32P, using standard techniques described by T. Maniatis, et al. in "Molecular Cloning", Cold Spring Harbor Press, p. 115 (1982).

The enzyme and the radiolabeled DNA are added together first, then drug is added. After an incubation period of 30 minutes, the mixtures are quenched using 1% SDS. The mixtures are then subjected to agarose gel electrophoresis which separates the full length, linear substrate DNA from any small fragments that might be formed as a consequence of drug action. Smaller fragments run with a higher mobility. The distribution of the DNA species in the gel is assessed by autoradiography as described by T. Maniatis, et al. in "Molecular Cloning", Cold Spring Harbor Press, p. 115 (1982).

DNA breakage activity is assessed based on the level of substrate lost, the level of DNA appearing as smaller pieces running faster in the gel, and the distribution of these smaller pieces in the gel. The last criterion is important since drug-induced DNA cleavage that is enzyme-mediated fragmentation results in specific banding patterns due to the fact that the enzyme binds to specific sequences along the DNA molecule. A definite banding pattern is thus indicative of topo II-mediated cleavage and correlates well with anti-tumor activity. The compounds of the present invention demonstrate the ability to induce this type of cleavage. The potencies of the compounds are estimated by comparing the extent of DNA cleavage at various concentrations of compound with the cleavage detectable at known concentrations of etoposide and teniposide, two anti-tumor agents that are known to act by inducing topo II mediated DNA cleavage. Concentrations of compound which cleave the DNA to smaller fragments are listed in Table 5.

TABLE 5

| Topoisomerase II-mediated DNA breakage | |
|---|---|
| Example No. | Concentration (µg/mL) |
| 1 | 32 (SB) |
| 2 | 32 (SB) |
| 3 | 32 (SB) |
| 4 | 32 (SB) |
| 5 | 64 (MB) |
| 6 | 32 (SB) |
| 7 | 32 (SB) |
| 8 | 32 (MB) |
| 9 | 32 (SB) |
| 10 | 32 (SB) |
| 11 | 32 (SB) |
| 12 | 32 (SB) |
| 14 | 64 (MB) |
| 15 | 128 (MB) |
| 16 | 32-64 (MB) |
| 17 | 32-64 (WB) |
| 19 | 64 (MB) |
| 20 | 64 (MB) |
| 22 | 128 (WB) |
| 23 | 32-128 (WB) |
| 25 | 64 (WB) |
| 29 | 128 (WB) |
| 32 | 64 (WB) |

SB = strong breakage; MB = moderate breakage; WB = weak breakage

In vitro Cytotoxicity Assays

The compounds of the present invention exhibited potent in vitro cytotoxic activity against tumor lines such as Hela and Lewis lung Carcinoma (LLCI) cells. The cytotoxicity of the compounds of the present invention is illustrated in Table 6. $IC_{50}$'s were measured in a colorimetric assay for cytotoxic activity against cultured cells according to the protocol described below:

A three day microtiter assay is used to measure the growth inhibition of cultured cells exposed to a range of drug concentrations. Metabolic activity is measured by the cell's ability to reduce the tetrazolium dye, MTT (3-(4,5-dimethylthiazol-2-yl)-2,5-diphenyltetrazolium bromide) to a quantifiable colored end-product, which absorbs at 570 nm in the visible spectrum. Surviving cells reduce the MTT dye.

Test compounds are dissolved in dimethyl sulfoxide (DMSO) and diluted, first with Earle's Balanced Salt Solution, followed by culture medium, to twice the highest concentration of compound to be tested. From this concentrated stock, two-fold serial dilutions are prepared in 96-well microtiter trays, each well containing twice the desired final concentration of compound. Each concentration is tested in triplicate and compared to triplicate drug-free controls.

The cells are grown in the same medium used for diluting the compounds. After harvesting by trypsinization*, viable cell counts are determined and cell density is adjusted to 25,000 cells/mL. Inoculum (0.1 mL), containing the cells, is then added to each well for a final concentration of 2,500 cells per well. Addition of the inoculum dilutes the test compounds to the desired final concentration.

*Adherent cells are harvested by trypsinization as follows:
1. Remove the medium by aspiration.
2. Rinse cell monolayer twice with Earle's Balanced Salt Solution.
3. Add trypsin (0.05%)/EDTA (0.53 mM). For each 25 cm² use approximately 0.2 mL of solution, tilt to cover the monolayer, then withdraw trypsin leaving only a thin film of solution. Incubate at room temperature until cell monolayer detaches.

4. When the cells have detached as determined by visual and/or microscopic observation, add medium containing fetal calf serum to stop the action of the trypsin and resuspend the cells. Triturate to aid dissociation of cell clumps.

5. Determine the number of cells per milliliter by electronic cell counter (e.g. Coulter Counter) or by mixing an aliquot of cell suspension with Trypan Blue (0.4% in normal saline) and counting the viable cells using a hemacytometer.

Microtiter trays are incubated for three days at 36° C. in a humidified atmosphere containing 5% carbon dioxide.

After three days, 20 microtiters of 5 mg/mL MTT in phosphate-buffered saline solution is added to each well. Trays are returned to the incubator for two to four hours to allow the surviving cells to reduce the dye. Medium and unreduced dye are removed by aspiration. DMSO is added to each well to dissolve the water insoluble, colored end product of the dye reduction so that it can be measured spectrophotometrically at 570 nm. The $IC_{50}$ is determined as the concentration of compound tested required to reduce the absorbance at 570 nm to 50% of non-drug treated control values.

TABLE 6

| | In vitro tumor cell cytotoxicity ($IC_{50}$ μg/mL) | | | | |
|---|---|---|---|---|---|
| Example No. | Hela[a] | LLC1[b] | P388.D1[c] | A549[d] | HCT-8[e] |
| 1 | 7.0 | — | — | — | — |
| 2 | 3.9 | 0.99 | — | — | — |
| 3 | — | — | 3.1 | 8.3 | 14.0 |
| 4 | 1.3 | — | — | — | — |
| 5 | 4.0 | — | — | — | — |
| 6 | — | — | 6.3 | 12.5 | — |
| 7 | — | — | 0.2 | — | — |
| 8 | 3.9 | — | — | — | — |
| 9 | — | — | 2.05 | 3.9 | — |
| 10 | — | — | 0.23 | 2.9 | — |
| 11 | 0.95 | 0.52 | — | — | — |
| 12 | — | — | <0.05 | 0.30 | — |
| 13 | 0.55 | — | — | — | — |
| 14 | 4.0 | 1.5 | — | — | — |
| Etoposide | 4.0 | — | 0.05 | 1.00 | 0.68 |

[a]Hela cells were acquired from ATCC, catalog #CCL2.
[b]LLC1 = Lewis Lung Carcinoma
[c]P388 D1 is a leukemia cell line.
[d]A549 is a human breast cancer cell line.
[e]HCT-8 is a human colon cancer cell line.

In Vivo Antitumor Activity

The in vivo data presented in Table 7 was determined in $BDF_1$ mice for two murine cancer models, using 6 to 10 animals per test group. In the case of Lewis Lung carcinoma (LL) the mice are inoculated subcutaneously (SC) in the axillary region with a puncture in the inguinal area with the tumor on day 0. The compound being tested is administered intraperitoneally (IP) from day 1 to day 9 for a total of nine injections. The tumors are weighed on day 14 and the weight inhibition expressed as the median weight ratio of treated (T) to control (C) tumors. In the case of P388 Leukemia cells, a suspension of diluted ascites fluid (0.1 mL) containing $1 \times 10^6$ cells is implanted IP into the mice on day 0 and the compound being tested is administered IP from day 1 to day 5 for a total of five injections. Survival was monitored for 30 days and the increased lifespan expressed as median survival time of treated (T) to control (C) mice.

TABLE 7

| | In vivo antitumor activity | | |
|---|---|---|---|
| Example No. | dose (mg/kg) | LL (T/C)[a] | P388 Leukemia % T/C[b] |
| 1 | 250 | | 108 |
| 1 | 125 | | 108 |

TABLE 7-continued

| | In vivo antitumor activity | | |
|---|---|---|---|
| Example No. | dose (mg/kg) | LL (T/C)[a] | P388 Leukemia % T/C[b] |
| 1 | 62.5 | | 100 |
| 1 | 31.25 | | 104 |
| 3 | 250 | 0.35 | 160 |
| 3 | 125 | 0.59 | 160 |
| 3 | 62.5 | 0.75 | 145 |
| 3 | 31.5 | 0.81 | 145 |
| 5 | 10 | | 142 |
| 5 | 5 | | 129 |
| 5 | 2.5 | | 125 |
| 5 | 12.5 | | 117 |
| 10 | 100 | | 117 |
| 10 | 50 | | 133 |
| 10 | 25 | | 133 |
| 10 | 12.5 | | 129 |

[a]determined on day 14
[b]median lifespan increase of treated compared to control mice.

This invention has been described in terms of specific embodiments set forth in detail. It should be understood, however, that these embodiments are presented by way of illustration only and that the invention is not necessarily limited thereto. Modifications and variations within the spirit and scope of the claims that follow can be made and will be readily apparent from this disclosure, as those skilled in the art will appreciate.

What is claimed is:

1. A method of treating a neoplastic disease selected from the group consisting of leukemia and lung, breast and colon cancers, comprising administering to a patient in need a therapeutically effective amount of a compound of the formula

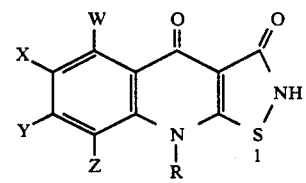

I which may exist in its tautomeric form

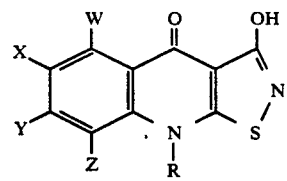

II wherein
R is selected from (a) lower alkyl, (b) haloalkyl, (c) lower cycloalkyl, (d) alkylamino, (e) an aromatic heterocyclic group and (f) a phenyl group;

W, X and Z are independently selected from hydrogen, halogen and lower alkyl; and Y is selected from (a) a phenyl group; (b) an amino group having the formula $-NR_2R_3$ wherein $R_2$ and $R_3$ are independently selected from hydrogen, lower alkyl, arylalkyl, hydrox-substituted loweralkyl, alkylamino, amino, aminoalkyl, a N-containing heterocyclic group and a bicyclic N-containing heterocyclic group, or $R_2$ and $R_3$ taken together form a N-containing heterocyclic group; (c) a bicyclic N-containing heterocyclic group; and (d) $OR_{10}$, wherein $R_{10}$ is selected from hydrogen, lower alkyl, and a phenyl group, the heterocyclic groups containing between one and three heteroatoms selected from S, O and N and being optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula —NR$_6$R$_7$ wherein R$_6$ and R$_7$ are independently selected from hydrogen, lower alkyl, an alpha-amino acid and a polypeptide residue of between two and five amino acids;

or any two of W, X, Y and Z taken together form a fused aromatic or heterocyclic group;

or a pharmaceutically acceptable salt, ester, amide or prodrug thereof.

2. A method according to claim 1 wherein R is lower cycloalkyl or lower alkyl; W is hydrogen; X is halogen; Z is hydrogen or halogen; and Y is an amino group having the formula —NR$_2$R$_3$ wherein R$_2$ and R$_3$ are independently selected from hydrogen, lower alkyl, arylalkyl, hydroxy-substituted loweralkyl, alkylamino, amino, aminoalkyl, a N-containing heterocyclic group and a bicyclic N-containing heterocyclic group, or R$_2$ and R$_3$ taken together form a N-containing heterocyclic group, the heterocyclic groups containing between one and three heteroatoms selected from S, O and N and being optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula —NR$_6$R$_7$ wherein R$_6$ and R$_7$ are independently selected from hydrogen, lower alkyl, an alpha-amino acid and a polypeptide residue of between two and five amino acids.

3. A method according to claim 2 wherein R is cyclopropyl or ethyl; Z is halogen; and Y is selected from piperazinyl, piperidinyl, pyrrolidinyl, morpholino and thiomorpholino, optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula —NR$_6$R$_7$ wherein R$_6$ and R$_7$ are independently selected from hydrogen, lower alkyl, an alpha-amino acid and a polypeptide residue of between two and five amino acids.

4. A method according to claim 2 wherein R is cyclopropyl or ethyl; Z is hydrogen; and Y is selected from piperazinyl, piperidinyl, pyrrolidinyl, morpholino and thiomorpholino, optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula —NR$_6$R$_7$ wherein R$_6$ and R$_7$ are independently selected from hydrogen, lower alkyl, an alpha-amino acid and a polypeptide residue of between two and five amino acids.

5. A method according to claim 1 wherein the compound is selected from the group consisting of:

9-cyclopropyl-6,8-difluoro-7-(1-piperazinyl)-2,3,4,9-tetrahydroisothiazolo[5,4-b]quinoline-3,4-dione;

9-cyclopropyl-6,8-difluoro-7-(3-methyl-1-piperazinyl)-2,3,4,9-tetrahydroisothiazolo[5,4-b]quinoline-3,4-dione;

9-cyclopropyl-6,8-difluoro-7-(4-methyl-1-piperazinyl)-2,3,4,9-tetrahydroisothiazolo[5,4-b]quinoline-3,4-dione;

9-cyclopropyl-6,8-difluoro-7-(4-(2'-hydroxy)ethyl-1-piperazinyl)-2,3,4,9-tetrahydroisothiazolo[5,4-b]quinoline-3,4-dione;

9-cyclopropyl-6,8-difluoro-7-(1-piperidinyl)-2,3,4,9-tetrahydroisothiazolo[5,4-b]quinoline-3,4-dione;

9-cyclopropyl-6,8-difluoro-7-(4-hydroxy-1-piperidinyl)-2,3,4,9-tetrahydroisothiazolo[5,4-b]quinoline-3,4-dione;

9-cyclopropyl-6,8-difluoro-7-(1-morpholino)-2,3,4,9-tetrahydroisothiazolo[5,4-b]quinoline-3,4-dione;

9-cyclopropyl-6,8-difluoro-7-(1-thiomorpholino)-2,3,4,9-tetrahydroisothiazolo[5,4-b]quinoline-3,4-dione;

9-cyclopropyl-6,8-difluoro-7-(1-diazepinyl)-2,3,4,9-tetrahydroisothiazolo[5,4-b]quinoline-3,4-dione;

9-cyclopropyl-6,8-difluoro-7-(3-amino-1-pyrrolidinyl)-2,3,4,9-tetrahydroisothiazolo[5,4-b]quinoline-3,4-dione;

9-cyclopropyl-6,8-difluoro-7-(3-aminomethyl-1-pyrrolidinyl)-2,3,4,9-tetrahydroisothiazolo[5,4-b]quinoline-3,4-dione;

9-cyclopropyl-6,8-difluoro-7-(4-chloro-3-aminomethyl-1-pyrrolidinyl)-2,3,4,9-tetrahydroisothiazolo[5,4-b]quinoline-3,4-dione;

9-cyclopropyl-6,8-difluoro-7-(1-piperazinyl)-2,3,4,9-tetrahydroisothiazolo[5,4-b]quinoline-3,4-dione;

9-cyclopropyl-6,8-difluoro-7-(3-ethylaminomethyl-1-pyrrolidinyl)-2,3,4,9-tetrahydroisothiazolo[5,4-b]quinoline-3,4-dione;

9-cyclopropyl-6,8-difluoro-7-(N-valyl-3-amino-1-pyrrolidinyl)-2,3,4,9-tetrahydroisothiazolo[5,4-b]quinoline-3,4-dione;

9-cyclopropyl-6,8-difluoro-7-(N-alanyl-3-amino-1-pyrrolidinyl)-2,3,4,9-tetrahydroisothiazolo[5,4-b]quinoline-3,4-dione;

9-cyclopropyl-6,8-difluoro-7-(N-glycyl-3-amino-1-pyrrolidinyl)-2,3,4,9-tetrahydroisothiazolo[5,4-b]quinoline-3,4-dione;

9-ethyl-6,8-difluoro-7-(1-piperazinyl)-2,3,4,9-tetrahydroisothiazolo[5,4-b]quinoline-3,4-dione;

9-ethyl-6,8-difluoro-7-(3-methyl-1-piperazinyl)-2,3,4,9-tetrahydroisothiazolo[5,4-b]quinoline-3,4-dione;

9-ethyl-6,8-difluoro-7-(4-methyl-1-piperazinyl)-2,3,4,9-tetrahydroisothiazolo[5,4-b]quinoline-3,4-dione;

9-ethyl-6,8-difluoro-7-(4-(2'-hydroxy)ethyl-1-piperazinyl)-2,3,4,9-tetrahydroisothiazolo[5,4-b]quinoline-3,4-dione;

9-ethyl-6,8-difluoro-7-(1-piperidinyl)-2,3,4,9-tetrahydroisothiazolo[5,4-b]quinoline-3,4-dione;

9-ethyl-6,8-difluoro-7-(4-hydroxy-1-piperidinyl)-2,3,4,9-tetrahydroisothiazolo[5,4-b]quinoline-3,4-dione;

9-ethyl-6,8-difluoro-7-(1-morpholino)-2,3,4,9-tetrahydroisothiazolo[5,4-b]quinoline-3,4-dione;

9-ethyl-6,8-difluoro-7-(1-thiomorpholino)-2,3,4,9-tetrahydroisothiazolo[5,4-b]quinoline-3,4-dione;

9-ethyl-6,8-difluoro-7-(1-diazepinyl)-2,3,4,9-tetrahydroisothiazolo[5,4-b]quinoline-3,4-dione;

9-ethyl-6,8-difluoro-7-(3-amino-1-pyrrolidinyl)-2,3,4,9-tetrahydroisothiazolo[5,4-b]quinoline-3,4-dione;

9-ethyl-6,8-difluoro-7-(3-aminomethyl-1-pyrrolidinyl)-2,3,4,9-tetrahydroisothiazolo[5,4-b]quinoline-3,4-dione;

9-ethyl-6,8-difluoro-7-(4-chloro-3-aminomethyl-1-pyrrolidinyl)-2,3,4,9-tetrahydroisothiazolo[5,4-b]quinoline-3,4-dione;

9-ethyl-6,8-difluoro-7-(1-piperazinyl)-2,3,4,9-tetrahydroisothiazolo[5,4-b]quinoline-3,4-dione;

9-ethyl-6,8-difluoro-7-(3-ethylaminomethyl-1-pyrrolidinyl)-2,3,4,9-tetrahydroisothiazolo[5,4-b]quinoline-3,4-dione;

9-ethyl-6,8-difluoro-7-(N-valyl-3-amino-1-pyrrolidinyl)-2,3,4,9-tetrahydroisothiazolo[5,4-b]quinoline-3,4-dione;

9-ethyl-6,8-difluoro-7-(N-alanyl-3-amino-1-pyrrolidinyl)-2,3,4,9-tetrahydroisothiazolo[5,4-b]quinoline-3,4-dione;

9-ethyl-6,8-difluoro-7-(N-glycyl-3-amino-1-pyrrolidinyl)-2,3,4,9-tetrahydroisothiazolo[5,4-b]quinoline-3,4-dione;

and pharmaceutically acceptable salts, esters, amides and prodrugs thereof.

6. A pharmaceutical composition having antineoplastic activity comprising a pharmaceutical carrier and a therapeutically effective amount of a compound having the formula which may exist in its tautomeric form wherein
R is selected from (a) lower alkyl, (b) haloalkyl, (c) lower cycloalkyl, (d) alkylamino, (e) an aromatic heterocyclic group and (f) a phenyl group;
W, X and Z are independently selected from hydrogen, halogen and lower alkyl; and
Y is selected from (a) a phenyl group; (b) an amino group having the formula —NR$_2$R$_3$ wherein R$_2$ and R$_3$ are independently selected from hydrogen, lower alkyl, arylalkyl, hydroxy-substituted lower-alkyl, alkylamino, amino, aminoalkyl, a N-containing heterocyclic group and a bicyclic N-containing heterocyclic group, or R$_2$ and R$_3$ taken together form a N-containing heterocyclic group; (c) a bicyclic N-containing heterocyclic group; and (d) OR$_{10}$, wherein R$_{10}$ is selected from hydrogen, lower alkyl, and a phenyl group, the heterocyclic groups containing between one and three heteroatoms selected from S, O and N and being optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula —NR$_6$R$_7$ wherein R$_6$ and R$_7$ are independently selected from hydrogen, lower alkyl, an alpha-amino acid and a polypeptide residue of between two and five amino acids;

or any two of W, X, Y and Z taken together form a fused aromatic or heterocyclic group;

or a pharmaceutically acceptable salt, ester, amide or prodrug thereof.

7. A compound having the formula which may exist in its tautomeric form wherein
R is selected from (a) lower alkyl, (b) haloalkyl, (c) lower cycloalkyl, (d) alkylamino, (e) an aromatic heterocyclic group and (f) a phenyl group;
W, X and Z are independently selected from hydrogen, halogen and lower alkyl; and
Y is selected from (a) a phenyl group; (b) an amino group having the formula —NR$_2$R$_3$ wherein R$_2$ and R$_3$ are independently selected from hydrogen, lower alkyl, arylalkyl, hydroxy-substituted lower-alkyl, alkylamino, amino, aminoalkyl, a N-containing heterocyclic group and a bicyclic N-containing heterocyclic group, or R$_2$ and R$_3$ taken together form a N-containing heterocyclic group; (c) a bicyclic N-containing heterocyclic group; and (d) OR$_{10}$, wherein R$_{10}$ is selected from hydrogen, lower alkyl, and a phenyl group, the heterocyclic groups containing between one and three heteroatoms selected from S, O and N and being optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula —NR$_6$R$_7$ wherein R$_6$ and R$_7$ are independently selected from hydrogen, lower alkyl, an alpha-amino acid and a polypeptide residue of between two and five amino acids;

or any two of W, X, Y and Z taken together form a fused aromatic or heterocyclic group;

or a pharmaceutically acceptable salt, ester, amide or prodrug thereof; with the proviso that when R is lower alkyl, lower cycloalkyl, alkylamino, an aromatic heterocyclic group or a phenyl group, W is hydrogen, X is fluoro and Z is either hydrogen or halogen, then Y is not $NR_2R_3$ wherein $R_2$ and $R_3$ are selected from lower alkyl, alkylamino, amino, and hydroxy-substituted lower alkyl or, taken together, $R_2$ and $R_3$ form a N-containing heterocyclic group.

8. A compound according to claim 7 wherein R is lower cycloalkyl or lower alkyl; W is hydrogen; X and Z are independently hydrogen or halogen; and Y is selected from $OR_{10}$, wherein $R_{10}$ is a phenyl group, and an amino group having the formula $-NR_2R_3$ wherein $R_2$ and $R_3$ are independently selected from hydrogen, lower alkyl, arylalkyl, hydroxy-substituted loweralkyl, alkylamino, amino, aminoalkyl, a N-containing heterocyclic group and a bicyclic N-containing heterocyclic group, or $R_2$ and $R_3$ taken together form a N-containing heterocyclic group, the heterocyclic groups containing between one and three heteroatoms selected from S, O and N and being optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula $-NR_6R_7$ wherein $R_6$ and $R_7$ are independently selected from hydrogen, lower alkyl, an alpha-amino acid and a polypeptide residue of between two and five amino acids; or Y taken together with X or Z forms a fused aromatic or heterocyclic group.

9. A compound according to claim 8 wherein R is cyclopropyl or ethyl; X is hydrogen or fluoro; Z is hydrogen or fluoro or chloro; and Y is selected from $OR_{10}$, wherein $R_{10}$ is a phenyl group, and an amino group having the formula $-NR_2R_3$ wherein $R_2$ and $R_3$ are independently selected from hydrogen, lower alkyl, arylalkyl, hydroxy-substituted loweralkyl, alkylamino, amino, aminoalkyl, a N-containing heterocyclic group and a bicyclic N-containing heterocyclic group, or $R_2$ and $R_3$ taken together form a N-containing heterocyclic group, the heterocyclic groups containing between one and three heteroatoms selected from S, O and N and being optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula $-NR_6R_7$ wherein $R_6$ and $R_7$ are independently selected from hydrogen, lower alkyl, an alpha-amino acid and a polypeptide residue of between two and five amino acids; or Y and Z taken together form a benzene ring or X and Y taken together form a methylene dioxy group.

10. A pharmaceutical composition comprising a pharmaceutically acceptable carrier and a therapeutically effective amount of a compound according to claim 7.

11. A method of inducing topoisomerase II-mediated DNA breakage in tumor cells of a human or lower animal host, comprising administering to the host an effective amount of a compound of the formula

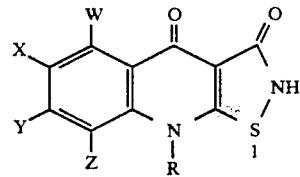

which may exist in its tautomeric form

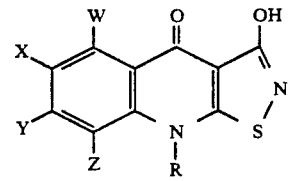

wherein
R is selected from (a) lower alkyl, (b) haloalkyl, (c) lower cycloalkyl, (d) alkylamino, (e) an aromatic heterocyclic group and (f) a phenyl group;
W, X and Z are independently selected from hydrogen, halogen and lower alkyl; and
Y is selected from (a) a phenyl group; (b) an amino group having the formula $-NR_2R_3$ wherein $R_2$ and $R_3$ are independently selected from hydrogen, lower alkyl, arylalkyl, hydroxy-substituted loweralkyl, alkylamino, amino, aminoalkyl, a N-containing heterocyclic group and a bicyclic N-containing heterocyclic group, or $R_2$ and $R_3$ taken together form a N-containing heterocyclic group; (c) a bicyclic N-containing heterocyclic group; and (d) $OR_{10}$, wherein $R_{10}$ is selected from hydrogen, lower alkyl, and a phenyl group, the heterocyclic groups containing between one and three heteroatoms selected from S, O and N and being optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula $-NR_6R_7$ wherein $R_6$ and $R_7$ are independently selected from hydrogen, lower alkyl, an alpha-amino acid and a polypeptide residue of between two and five amino acids;
or any two of W, X, Y and Z taken together form a fused aromatic or heterocyclic group;
or a pharmaceutically acceptable salt, ester, amide or prodrug thereof.

12. A method according to claim 11 wherein R is lower cycloalkyl or lower alkyl; W is hydrogen; X is halogen; Z is hydrogen or halogen; and Y is an amino group having the formula $-NR_2R_3$ wherein $R_2$ and $R_3$ are independently selected from hydrogen, lower alkyl, arylalkyl, hydroxy-substituted loweralkyl, alkylamino, amino, aminoalkyl, a N-containing heterocyclic group and a bicyclic N-containing heterocyclic group, or $R_2$ and $R_3$ taken together form a N-containing heterocyclic group, the heterocyclic groups containing between one and three heteroatoms selected from S, O and N and being optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula —NR$_6$R$_7$ wherein R$_6$ and R$_7$ are independently selected from hydrogen, lower alkyl, an alpha-amino acid and a polypeptide residue of between two and five amino acids.

13. A method according to claim 12 wherein R is cyclopropyl or ethyl; Z is halogen; and Y is selected from piperazinyl, piperidinyl, pyrrolidinyl, morpholino and thiomorpholino, optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula —NR$_6$R$_7$ wherein R$_6$ and R$_7$ are independently selected from hydrogen, lower alkyl, an alpha-amino acid and a polypeptide residue of between two and five amino acids.

14. A method according to claim 12 wherein R is cyclopropyl or ethyl; Z is hydrogen; and Y is selected from piperazinyl, piperidinyl, pyrrolidinyl, morpholino, and thiomorpholino, optionally substituted with up to three substituents independently selected from halogen, hydroxy, lower alkoxy, lower alkyl, hydroxy-substituted lower alkyl, amino, alkylamino, aminoalkyl, arylalkyl, alkanoylamino, an alpha-amino acid, a polypeptide residue of between two and five amino acids, and an amino group having the formula —NR$_6$R$_7$ wherein R$_6$ and R$_7$ are independently selected from hydrogen, lower alkyl, an alpha-amino acid and a polypeptide residue of between two and five amino acids.

15. A method according to claim 11 wherein the compound is selected from the group consisting of:

9-cyclopropyl-6,8-difluoro-7-(1-piperazinyl)-2,3,4,9-tetrahydroisothiazolo[5,4-b]quinoline-3,4-dione;
9-cyclopropyl-6,8-difluoro-7-(3-methyl-1-piperazinyl)-2,3,4,9-tetrahydroisothiazolo[5,4-b]quinoline-3,4-dione;
9-cyclopropyl-6,8-difluoro-7-(4-methyl-1-piperazinyl)-2,3,4,9-tetrahydroisothiazolo[5,4-b]quinoline-3,4-dione;
9-cyclopropyl-6,8-difluoro-7-(4-(2'-hydroxy)ethyl-1-piperazinyl)-2,3,4,9-tetrahydroisothiazolo[5,4-b]quinoline-3,4-dione;
9-cyclopropyl-6,8-difluoro-7-(1-piperidinyl-2,3,4,9-tetrahydroisothiazolo[5,4-b]quinoline-3,4-dione;
9-cyclopropyl-6,8-difluoro-7-(4-hydroxy-1-piperidinyl)-2,3,4,9-tetrahydroisothiazolo[5,4-b]quinoline-3,4-dione;
9-cyclopropyl-6,8-difluoro-7-(1-morpholino)-2,3,4,9-tetrahydroisothiazolo[5,4-b]quinoline-3,4-dione;
9-cyclopropyl-6,8-difluoro-7-(1-thiomorpholino)-2,3,4,9-tetrahydroisothiazolo[5,4-b]quinoline-3,4-dione;
9-cyclopropyl-6,8-difluoro-7-(1-diazepinyl)-2,3,4,9-tetrahydroisothiazolo[5,4-b]quinoline-3,4-dione;
9-cyclopropyl-6,8-difluoro-7-(3-amino-1-pyrrolidinyl)-2,3,4,9-tetrahydroisothiazolo[5,4-b]quinoline-3,4-dione;
9-cyclopropyl-6,8-difluoro-7-(3-aminomethyl-1-pyrrolidinyl)-2,3,4,9-tetrahydroisothiazolo[5,4-b]quinoline-3,4-dione;
9-cyclopropyl-6,8-difluoro-7-(4-chloro-3-aminomethyl-1-pyrrolidinyl)-2,3,4,9-tetrahydroisothiazolo[5,4-b]quinoline-3,4-dione;
9-cyclopropyl-6,8-difluoro-7-(1-piperazinyl)-2,3,4,9-tetrahydroisothiazolo[5,4-b]quinoline-3,4-dione;
9-cyclopropyl-6,8-difluoro-7-(3-ethylaminomethyl-1-pyrrolidinyl)-2,3,4,9-tetrahydroisothiazolo[5,4-b]quinoline-3,4-dione;
9-cyclopropyl-6,8-difluoro-7-(N-valyl-3-amino-1-pyrrolidinyl)-2,3,4,9-tetrahydroisothiazolo[5,4-b]quinoline-3,4-dione;
9-cyclopropyl-6,8-difluoro-7-(N-alanyl-3-amino-1-pyrrolidinyl)-2,3,4,9-tetrahydroisothiazolo[5,4-b]quinoline-3,4-dione;
9-cyclopropyl-6,8-difluoro-7-(N-glycyl-3-amino-1-pyrrolidinyl)-2,3,4,9-tetrahydroisothiazolo[5,4-b]quinoline-3,4-dione;
9-ethyl-6,8-difluoro-7-(1-piperazinyl)-2,3,4,9-tetrahydroisothiazolo[5,4-b]quinoline-3,4-dione;
9-ethyl-6,8-difluoro-7-(3-methyl-1-piperazinyl)2,3,4,9-tetrahydroisothiazolo[5,4-b]quinoline-3,4-dione;
9-ethyl-6,8-difluoro-7-(4-methyl-1-piperazinyl)2,3,4,9-tetrahydroisothiazolo[5,4-b]quinoline-3,4-dione;
9-ethyl-6,8-difluoro-7-(4-(2'-hydroxy)ethyl-1-piperazinyl)-2,3,4,9-tetrahydroisothiazolo[5,4-b]quinoline-3,4-dione;
9-ethyl-6,8-difluoro-7-(1-piperidinyl)-2,3,4,9-tetrahydroisothiazolo[5,4-b]quinoline-3,4-dione;
9-ethyl-6,8-difluoro-7-(4-hydroxy-1-piperidinyl)-2,3,4,9-tetrahydroisothiazolo[5,4-b]quinoline-3,4-dione;
9-ethyl-6,8-difluoro-7-(1-morpholino)-2,3,4,9-tetrahydroisothiazolo[5,4-b]quinoline-3,4-dione;
9-ethyl-6,8-difluoro-7-(1-thiomorpholino)-2,3,4,9-tetrahydroisothiazolo[5,4-b]quinoline-3,4-dione;
9-ethyl-6,8-difluoro-7-(1-diazepinyl)-2,3,4,9-tetrahydroisothiazolo[5,4-b]quinoline-3,4-dione;
9-ethyl-6,8-difluoro-7-(3-amino-1-pyrrolidinyl)-2,3,4,9-tetrahydroisothiazolo[5,4-b]quinoline-3,4-dione;
9-ethyl-6,8-difluoro-7-(3-aminomethyl-1-pyrrolidinyl)-2,3,4,9-tetrahydroisothiazolo[5,4-b]quinoline-3,4-dione;
9-ethyl-6,8-difluoro-7-(4-chloro-3-aminomethyl-1-pyrrolidinyl)-2,3,4,9-tetrahydroisothiazolo[5,4-b]quinoline-3,4-dione;
9-ethyl-6,8-difluoro-7-(1-piperazinyl)-2,3,4,9-tetrahydroisothiazolo[5,4-b]quinoline-3,4-dione;
9-ethyl-6,8-difluoro-7-(3-ethylaminomethyl-1-pyrrolidinyl)-2,3,4,9-tetrahydroisothiazolo[5,4-b]quinoline-3,4-dione;
9-ethyl-6,8-difluoro-7-(N-valyl-3-amino-1-pyrrolidinyl)-2,3,4,9-tetrahydroisothiazolo[5,4-b]quinoline-3,4-dione;
9-ethyl-6,8-difluoro-7-(N-alanyl-3-amino-1-pyrrolidinyl)-2,3,4,9-tetrahydroisothiazolo[5,4-b]quinoline-3,4-dione;
9-ethyl-6,8-difluoro-7-(N-glycyl-3-amino-1-pyrrolidinyl)-2,3,4,9-tetrahydroisothiazolo[5,4-b]quinoline-3,4-dione;

and pharmaceutically acceptable salts, esters, amides and prodrugs thereof.

* * * * *